(12) United States Patent
Cool et al.

(10) Patent No.: US 8,722,398 B2
(45) Date of Patent: May 13, 2014

(54) TREATMENT OF BONE FRACTURE

(75) Inventors: Simon Cool, Immunos (SG); Victor Nurcombe, Immunos (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/518,186

(22) PCT Filed: Dec. 22, 2010

(86) PCT No.: PCT/SG2010/000481
§ 371 (c)(1),
(2), (4) Date: Jun. 21, 2012

(87) PCT Pub. No.: WO2011/078799
PCT Pub. Date: Jun. 30, 2011

(65) Prior Publication Data
US 2012/0301442 A1        Nov. 29, 2012

Related U.S. Application Data

(60) Provisional application No. 61/288,927, filed on Dec. 22, 2009.

(51) Int. Cl.
*C12N 5/00* (2006.01)
*A01N 63/00* (2006.01)

(52) U.S. Cl.
USPC .......................................... 435/325; 424/93.1

(58) Field of Classification Search
USPC ........................................ 435/325; 424/93.1
See application file for complete search history.

(56) References Cited

U.S. PATENT DOCUMENTS 6,541,024 B1 *   4/2003   Kadiyala et al. .............. 424/426
2009/0148420 A1   6/2009   Cool et al.

FOREIGN PATENT DOCUMENTS

| SG | 2010/011185 | * | 1/2010 | ............... C12N 5/06 |
|---|---|---|---|---|
| WO | 2006/085209 A1 | | 8/2006 | |
| WO | 2010/011185 A1 | | 1/2010 | |
| WO | 2010/030241 A1 | | 3/2010 | |
| WO | 2010/030244 A1 | | 3/2010 | |

OTHER PUBLICATIONS

Undale et al., "Mesenchymal Stem Cells for Bone Repair and Metabolic Bone Diseases", Mayo Clin Proc., 2009; 84 (10): 893-902.

* cited by examiner

*Primary Examiner* — Karen Cochrane Carlson
*Assistant Examiner* — Natalie Moss
(74) *Attorney, Agent, or Firm* — Choate, Hall & Stewart LLP; Charles E. Lyon

(57) ABSTRACT

The use of mesenchymal stem cells cultured in the presence of HS-2 for the treatment of bone fracture. Repair of bone fracture using such cells is enhanced compared with the treatment of bone fracture using mesenchymal cells cultured without HS-2. These mesenchymal stem cells may be formulated in a pharmaceutical composition and injected directly into tissues surrounding the fracture or used in a biocompatible implant or prosthesis.

16 Claims, 28 Drawing Sheets

| CONDITION | E 10 |
|---|---|
| pronase | 40,000 |
| mild alkali treatment | 25,000 |
| heparinase | 7,000 |
| number of heparinase resistant domains | 2 |

Figure 9

| | % E10 |
|---|---|
| TREATMENT | |
| Heparitinase | 61.5 |
| Heparinase | 15.3 |
| $HNO_2$ | 49.0 |

Figure 10

|  | %E10 GAG |
|---|---|
| DISACCHARIDE |  |
| IdoA/GlcA-AMann$_R$ | 12.9 |
| IdoA(2S)-AMann$_R$ | 53.4 |
| GlcA-AMann$_R$(6S) | 10.25 |
| IdoA-AMann$_R$(6S) | 3.4 |
| IdoA(2S)-AMann$_R$(6S) | 18.7 |
| GlcA(2S)-AMann$_R$ | 1.0 |
| GlcA-AMann$_R$(3S) | 0.30 |
| GlcA- AMann$_R$(3,6S) | 0.15 |
| UNKNOWN | 0.0 |

Figure 11

|  | % IN E10 |
|---|---|
| sulfation number : peak number |  |
| Non-sulfated : 1 | 37.2 |
| Mono-sulfated : 1 | 1.5 |
| Mono-sulfated : 2 | 1.0 |
| Mono-sulfated : 3 | 0.3 |
| Mono-sulfated : 4 | 0.3 |
| Mono-sulfated : 5 | 7.7 |
| Mono-sulfated : 6 | 23.9 |
| Mono-sulfated : 7 | 18.4 |
| Mono-sulfated : 8 | 0.7 |
| Mono-sulfated : 9 | 0.4 |
| Di-sulfated : 1 | 1.8 |
| Di-sulfated : 2 | 0.9 |
| Di-sulfated : 3 | 2.7 |
| Di-sulfated : 4 | 1.5 |
| Tri-sulfated : 1 | 1.0 |
| Tri-sulfated : 2 | 0.0 |
| Tri-sulfated : 3 | 0.3 |
| Tri-sulfated : 4 | 0.4 |
| TOTAL | 100 |

Figure 12

| PEAK NUMBER | DISACCHARIDE | % in E10 GAG |
|---|---|---|
| 1 | ΔHexUA-GlcNAc | 44.8 |
| 3 | ΔHexUA-GlcNSO$_3$ | 21.5 |
| 2 | ΔHexUA-GlcNAc(6S) | 8.0 |
| 7 | ΔHexUA(2S)-GlcNAc | 2.4 |
| 4 | ΔHexUA-GlcNSO$_3$(6S) | 4.0 |
| 5 | ΔHexUA(2S)-GlcNSO$_3$ | 12.4 |
| 8 | ΔHexUA(2S)-GlcNAc(6S) | 0.2 |
| 6 | ΔHexUA(2S)-GlcNSO$_3$(6S) | 4.1 |
| 9 | unknown | 2.4 |

Figure 13

| SULFATION | % in E10 GAG |
|---|---|
| Total sulfation/100 disaccharides | 77.4 |
| 6-O-Sulfate | 16.3 |
| 2-O-Sulfate | 19.1 |
| N-Sulfate | 42.0 |
| O-Sulfate | 35.4 |
| ratios of sulfations | |
| 2-O-Sulfate/6-O-Sulfate | 1.17 |
| N-Sulfate/O-Sulfate | 1.19 |
| N-Sulfate/2-O-Sulfate | 2.2 |
| N-Sulfate/6-Sulfate | 2.58 |

Figure 14

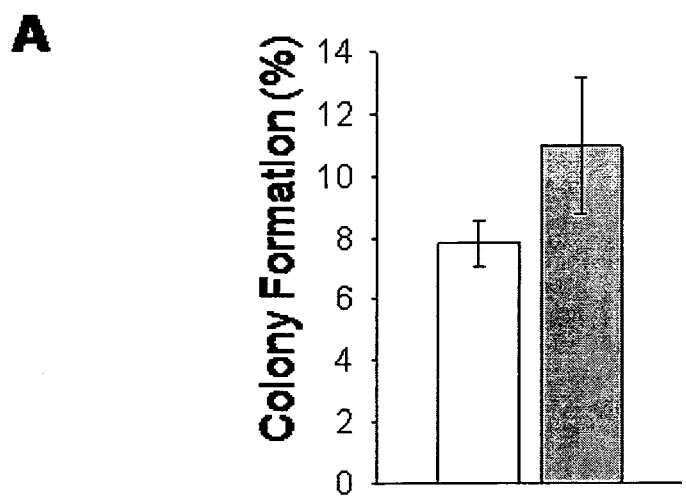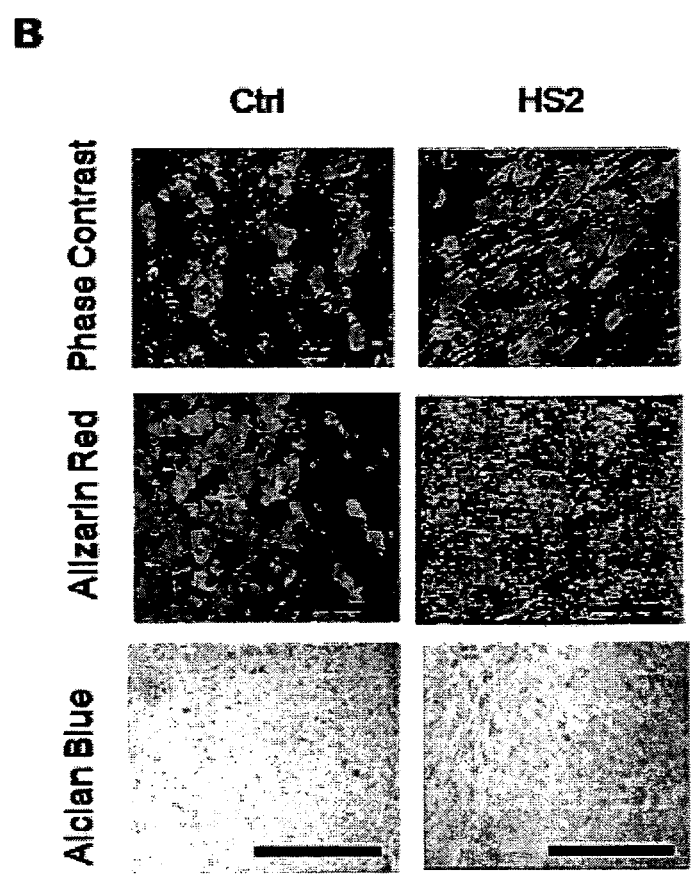
Figure 18

B

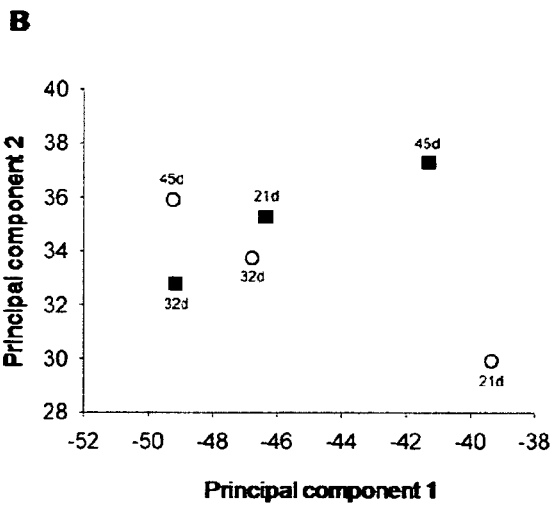

C

| Symbol | Description | Fold Change |
|---|---|---|
| Up regulated | | |
| VCAM1 | Vascular cell adhesion molecule 1 | 5.858986499 |
| GCM2 | Glial cells missing homolog 2 (Drosophila) | 5.695428926 |
| IGF2R | Insulin-like growth factor 2 receptor | 4.222693908 |
| ITGA4 | Integrin, alpha 4 (antigen CD49D, alpha 4 subunit of VLA-4 receptor) | 4.138188185 |
| CTNNAL1 | Catenin (cadherin-associated protein), alpha-like 1 | 4.042307815 |
| MYL4 | Myosin, light polypeptide 4, alkali; atrial, embryonic | 3.707959606 |
| LASS1 | LAG1 longevity assurance homolog 1 (S. cerevisiae) | 3.385028243 |
| ITGA2 | Integrin, alpha 2 (CD49B, alpha 2 subunit of VLA-2 receptor) | 3.37002629 |
| ICAM5 | Intercellular adhesion molecule 5, telencephalin | 3.231415232 |
| NCAM2 | Neural cell adhesion molecule 2 | 3.214941542 |
| NEUROG1 | Neurogenin 1 | 3.200451234 |
| FGF17 | Fibroblast growth factor 17 | 3.153615349 |
| FGF19 | Fibroblast growth factor 19 | 3.096687725 |
| SLC1A2 | Solute carrier family 1 (glial high affinity glutamate transporter), member 2 | 3.085489342 |
| FGF12 | Fibroblast growth factor 12 | 3.031896211 |
| Down regulated | | |
| FZD1 | Frizzled homolog 1 (Drosophila) | 105.5488977 |
| FZD3 | Frizzled homolog 3 (Drosophila) | 29.59892173 |
| GDF9 | Growth differentiation factor 9 | 28.11525787 |
| IL6R | Interleukin 6 receptor | 24.17353641 |
| IL6ST | Interleukin 6 signal transducer (gp130, oncostatin M receptor) | 22.10213584 |
| BMP5 | Bone morphogenetic protein 5 | 17.62639701 |
| TGFBR2 | Transforming growth factor, beta receptor II (70/80kDa) | 14.61376967 |
| FABP4 | Fatty acid binding protein 4, adipocyte | 12.70374367 |
| GJA7 | Gap junction protein, alpha 7, 45kDa (connexin 45) | 11.84183258 |
| GFAP | Glial fibrillary acidic protein | 11.73796254 |
| FZD4 | Frizzled homolog 4 (Drosophila) | 10.5989069 |
| CD9 | CD9 antigen (p24) | 8.572876617 |
| FABP7 | Fatty acid binding protein 7, brain | 8.416440381 |
| FABP7 | Fatty acid binding protein 7, brain | 8.416440381 |
| ACTA2 | Actin, alpha 2, smooth muscle, aorta | 8.135049403 |
| GDF8 | Growth differentiation factor 8 | 7.861982352 |
| NKX2-5 | NK2 transcription factor related, locus 5 (Drosophila) | 7.29208558 |
| FABP6 | Fatty acid binding protein 6, ileal (gastrotropin) | 7.247190687 |
| FZD7 | Frizzled homolog 7 (Drosophila) | 7.184131073 |

Figure 19 cont...

A)
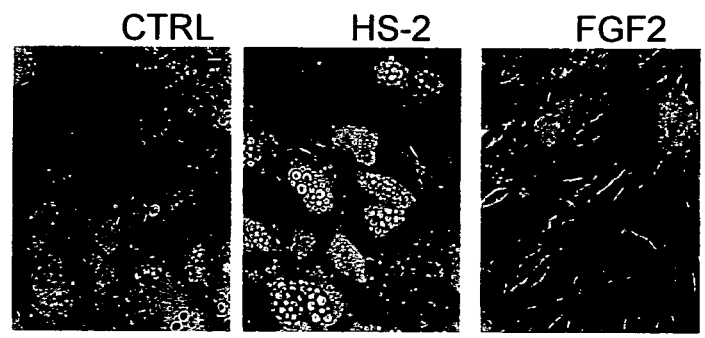
B)
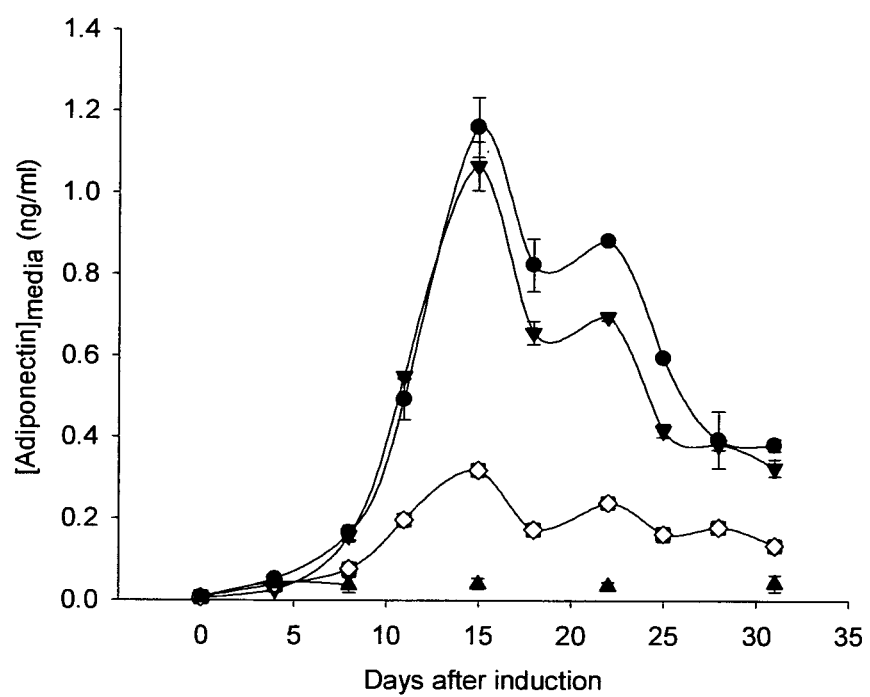
Figure 23

A)
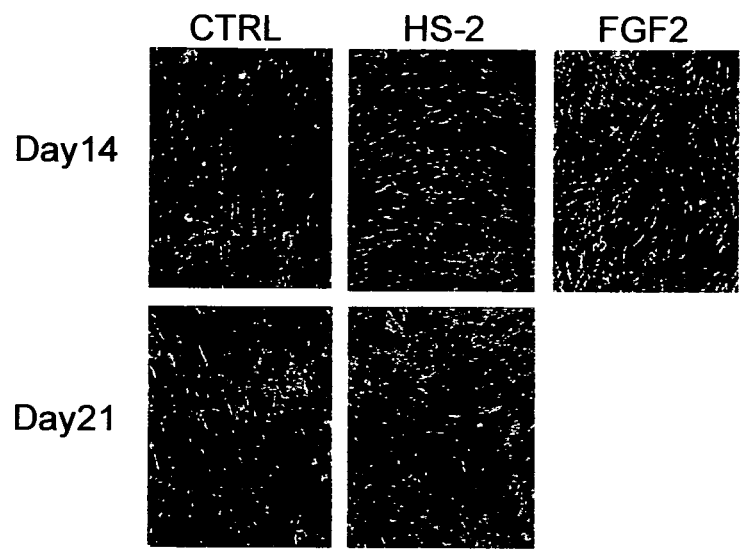
B)
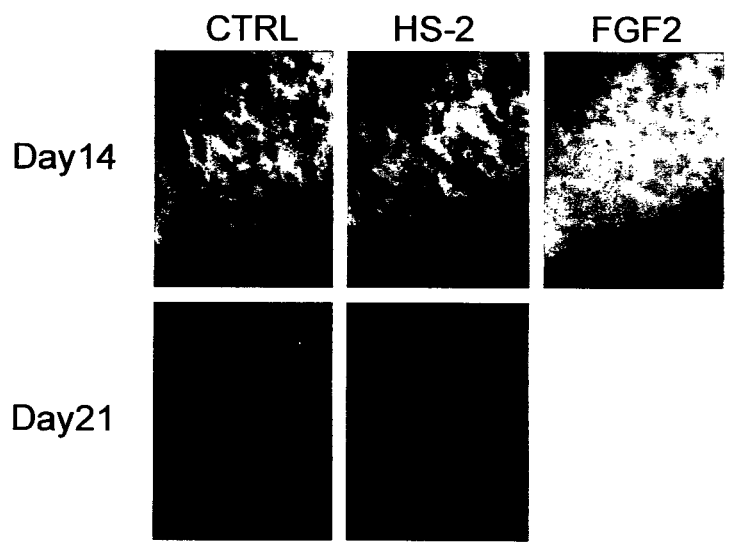
Figure 24

| Gene | Primers | Probe | ACC number |
|---|---|---|---|
| 18S | F: TTCGAGGCCCTGTAATTGGA | AGTCCACTTTAAATCCTT | AY248756 |
| | R: GCAGCAACTTTAATATACGCTATTGG | | |
| AlkPhos | F: ATGCCCTGGAGCTTCAGAAG | acgtTGgCtAaGaAtGtCaTc | NM_000478 |
| | R: TGGTGGAGCTGACCCTTGAG | | |
| BSPII | F: AGAGGAAGCAATCACCAAAATGA | ctgCtTTaaTtTtgCtCagc | NM_004967 |
| | R: TTGAGAAAGCACAGGCCATTC | | |
| ALBP | F: GGAAAGTCAAGAGCACCATAACCT | aaatCaAcCaCcaTaAaGaGa | BC003672.1 |
| | R: TTCCACCACCAGTTTATCATCCT | | |
| C/EBPα | F: GAGGGACCGGAGTTATGACAAG | aataTtTtGcTtTatCaGcCgat | NM_004364.2 |
| | R: GGCACAGAGGCCAGATACAAG | | |
| Coll2a | F: GTACTTTCCAATCTCAGTCACTCTAGGA | ccCcTCtCTttCTaAgaga | NM_033150 |
| | R: TTTTATTTTGCAGTCTGCCCAGTT | | |
| SOX9 | F: AAAGGCAACTCGTACCCAAATTT | caAgaCaCaAaCAtgAcc | Z46629 |
| | R: AGTGGGTAATGCGCTTGGAT | | |

Figure 25

| Table S2 | No. | Unigene | RefSeq # | Symbol | Description |
|---|---|---|---|---|---|
| | 1 | Hs.522891 | NM_000609 | CXCL12 | Chemokine (C-X-C motif) ligand 12 (stromal cell-derived factor 1) |
| | 2 | Hs.471119 | NM_001204 | BMPR2 | Bone morphogenetic protein receptor, type II (serine/threonine kinase) |
| Cluster 1 | 3 | Hs.453951 | NM_013957 | NRG1 | Neuregulin 1 |
| | 4 | Hs.429052 | NM_002211 | ITGB1 | Integrin, beta 1 (fibronectin receptor, beta polypeptide, antigen CD29 includes MDF2, MSK12) |
| | 5 | Hs.420269 | NM_001849 | COL6A2 | Collagen, type VI, alpha 2 |
| | 6 | Hs.369849 | NM_002392 | MDM2 | Mdm2, transformed 3T3 cell double minute 2, p53 binding protein (mouse) |

| Table S2 | No. | Unigene | RefSeq # | Symbol | Description |
|---|---|---|---|---|---|
| | 7 | Hs.470316 | NM_001105 | ACVR1 | Activin A receptor, type I |
| | 8 | Hs.513609 | NM_005611 | RBL2 | Retinoblastoma-like 2 (p130) |
| | 9 | Hs.74615 | NM_006206 | PDGFRA | Platelet-derived growth factor receptor, alpha polypeptide |
| | 10 | Hs.502328 | NM_000610 | CD44 | CD44 antigen (homing function and Indian blood group system) |
| Cluster 1 | 11 | Hs.28792 | NM_002192 | INHBA | Inhibin, beta A (activin A, activin AB alpha polypeptide) |
| | 12 | Hs.500483 | NM_001613 | ACTA2 | Actin, alpha 2, smooth muscle, aorta |
| | 13 | Hs.467824 | NM_015317 | PUM2 | Pumilio homolog 2 (Drosophila) |
| | 14 | Hs.436873 | NM_002210 | ITGAV | Integrin, alpha V (vitronectin receptor, alpha polypeptide, antigen CD51) |
| | 15 | Hs.532082 | NM_002184 | IL6ST | Interleukin 6 signal transducer (gp130, oncostatin M receptor) |
| | 16 | Hs.516105 | NM_001615 | ACTG2 | Actin, gamma 2, smooth muscle, enteric |
| | 17 | Hs.95577 | NM_000075 | CDK4 | Cyclin-dependent kinase 4 |
| | 18 | Hs.201671 | NM_005686 | SOX13 | SRY (sex determining region Y)-box 13 |
| | 19 | Hs.521461 | NM_006158 | NEFL | Neurofilament, light polypeptide 68kDa |
| | 20 | Hs.238990 | NM_004064 | CDKN1B | Cyclin-dependent kinase inhibitor 1B (p27, Kip1) |
| Cluster 2 | 21 | Hs.73793 | NM_003376 | VEGF | Vascular endothelial growth factor |
| | 22 | Hs.244723 | NM_001238 | CCNE1 | Cyclin E1 |
| | 23 | Hs.512234 | NM_000600 | IL6 | Interleukin 6 (interferon, beta 2) |
| | 24 | Hs.527971 | NM_006617 | NES | Nestin |
| | 25 | Hs.376032 | NM_002607 | PDGFA | Platelet-derived growth factor alpha polypeptide |

Figure 28

|  | 26 | Hs.125331 | XM_291161 | Dppa5 | Similar to developmental pluripotency associated 5; embryonal stem cell specific gene 1 |
|---|---|---|---|---|---|
|  | 27 | Hs.482390 | NM_003243 | TGFBR3 | Transforming growth factor, beta receptor III (betaglycan, 300kDa) |
|  | 28 | Hs.37092 | NM_005247 | FGF3 | Fibroblast growth factor 3 (murine mammary tumor virus integration site (v-int-2) oncogene homolog) |
| Cluster 3 | 29 | Hs.370414 | NM_018055 | NODAL | Nodal homolog (mouse) |
|  | 30 | Hs.408528 | NM_000321 | RB1 | Retinoblastoma 1 (including osteosarcoma) |
|  | 31 | Hs.46366 | NM_000614 | CNTF | Ciliary neurotrophic factor |
|  | 32 | Hs.133421 | NM_002310 | LIFR | Leukemia inhibitory factor receptor |
|  | 33 | Hs.95582 | NM_006942 | SOX15 | SRY (sex determining region Y)-box 15 |

Figure 28 cont...

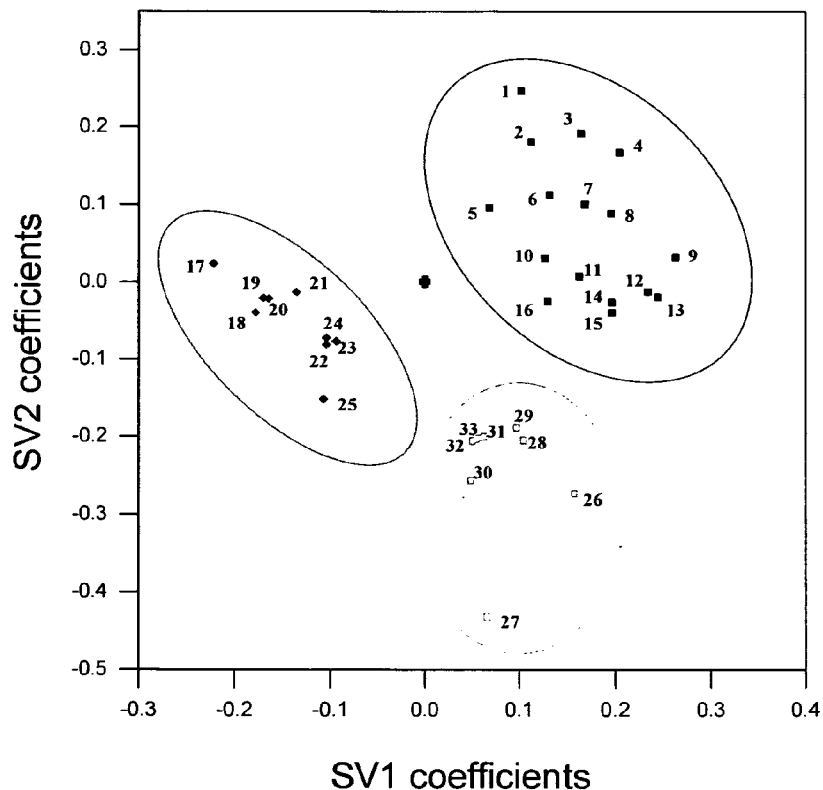

Figure 29

| Table S3 | Estimate ( )[a] | Lower CL[b] | Upper CL[c] |
|---|---|---|---|
| Ctrl-d45 vs Ctrl-d21 | 3.704 | 3.018 | 4.416 |
| Ctrl-d45 vs Ctrl-d21 | 5.373 | 4.976 | 5.744 |
| HS-2-d21 vs Ctrl-d21 | 8.761 | 7.921 | 9.653 |
| HS-2-d32 vs Ctrl-d21 | 1.57 | 1.28 | 1.844 |
| HS-2-d45 vs Ctrl-d21 | 3.008 | 2.758 | 3.328 |

Figure 32

SEQUENCE LISTING

<160> NUMBER OF SEQ ID NOS: 21

<210> SEQ ID NO 1
<211> LENGTH: 20
<212> TYPE: DNA
<213> ORGANISM: Artificial sequence
<220> FEATURE:

```
<223> OTHER INFORMATION: Synthetic sequence: Forward primer

<400> SEQUENCE: 1
ttcgaggccc tgtaattgga                                                 20

<210> SEQ ID NO 2
<211> LENGTH: 26
<212> TYPE: DNA
<213> ORGANISM: Artificial sequence
<220> FEATURE:
<223> OTHER INFORMATION: Synthetic sequence: Reverse primer

<400> SEQUENCE: 2
gcagcaactt taatatacgc tattgg                                          26

<210> SEQ ID NO 3
<211> LENGTH: 18
<212> TYPE: DNA
<213> ORGANISM: Artificial sequence
<220> FEATURE:
<223> OTHER INFORMATION: Synthetic sequence: Probe

<400> SEQUENCE: 3
agtccacttt aaatcctt                                                   18

<210> SEQ ID NO 4
<211> LENGTH: 20
<212> TYPE: DNA
<213> ORGANISM: Artificial sequence
<220> FEATURE:
<223> OTHER INFORMATION: Synthetic sequence: Forward primer

<400> SEQUENCE: 4
atgccctgga gcttcagaag                                                 20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 5
tggtggagct gacccttgag                                                 20

<210> SEQ ID NO 6
<211> LENGTH: 21
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 5, 6, 8, 10, 12, 14, 16, 18, 20
<223> OTHER INFORMATION: LNA base

<400> SEQUENCE: 6
acgttggcta agaatgtcat c                                               21

<210> SEQ ID NO 7
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 7
```
agaggaagca atcaccaaaa tga                                          23

<210> SEQ ID NO 8
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 8
ttgagaaagc acaggccatt c                                            21

<210> SEQ ID NO 9
<211> LENGTH: 20
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 4, 6, 7, 10, 12, 15, 17
<223> OTHER INFORMATION: LNA base

<400> SEQUENCE: 9
ctgctttaat tttgctcagc                                              20

<210> SEQ ID NO 10
<211> LENGTH: 24
<212> TYPE: DNA
<213> ORGANISM: Artificial sequence
<220> FEATURE:
<223> OTHER INFORMATION: Synthetic sequence: Forward primer

<400> SEQUENCE: 10
ggaaagtcaa gagcaccata acct                                         24

<210> SEQ ID NO 11
<211> LENGTH: 23
<212> TYPE: DNA
<213> ORGANISM: Artificial sequence
<220> FEATURE:
<223> OTHER INFORMATION: Synthetic sequence: Reverse primer

<400> SEQUENCE: 11
ttccaccacc agtttatcat cct                                          23

<210> SEQ ID NO 12
<211> LENGTH: 21
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 5, 7, 9, 11, 14, 16, 18, 20
<223> OTHER INFORMATION: LNA base

<400> SEQUENCE: 12
aaatcaacca ccataaagag a                                            21

<210> SEQ ID NO 13
<211> LENGTH: 22
<212> TYPE: DNA
<213> ORGANISM: Artificial sequence
<220> FEATURE:
<223> OTHER INFORMATION: Synthetic sequence: Forward primer

<400> SEQUENCE: 13

```
gagggaccgg agttatgaca ag                                              22

<210> SEQ ID NO 14
<211> LENGTH: 21
<212> TYPE: DNA
<213> ORGANISM: Artificial sequence
<220> FEATURE:
<223> OTHER INFORMATION: Synthetic sequence: Reverse primer

<400> SEQUENCE: 14
ggcacagagg ccagatacaa g                                               21

<210> SEQ ID NO 15
<211> LENGTH: 23
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 5, 7, 9, 11, 13, 16, 20
<223> OTHER INFORMATION: LNA base

<400> SEQUENCE: 15
aatattttgc tttatcagcc gat                                             23

<210> SEQ ID NO 16
<211> LENGTH: 28
<212> TYPE: DNA
<213> ORGANISM: Artificial sequence
<220> FEATURE:
<223> OTHER INFORMATION: Synthetic sequence: Forward primer

<400> SEQUENCE: 16
gtactttcca atctcagtca ctctagga                                        28

<210> SEQ ID NO 17
<211> LENGTH: 24
<212> TYPE: DNA
<213> ORGANISM: Artificial sequence
<220> FEATURE:
<223> OTHER INFORMATION: Synthetic sequence: Reverse primer

<400> SEQUENCE: 17
ttttattttg cagtctgccc agtt                                            24

<210> SEQ ID NO 18
<211> LENGTH: 19
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 3, 5, 6, 8, 9, 12, 13, 15
<223> OTHER INFORMATION: LNA base

<400> SEQUENCE: 18
cccctctctt tctaagaga                                                  19

<210> SEQ ID NO 19
<211> LENGTH: 23
<212> TYPE: DNA
<213> ORGANISM: Artificial sequence
<220> FEATURE:
<223> OTHER INFORMATION: Synthetic sequence: Forward primer

<400> SEQUENCE: 19
```

-continued

```
aaaggcaact cgtacccaaa ttt                                        23

<210> SEQ ID NO 20
<211> LENGTH: 20
<212> TYPE: DNA
<213> ORGANISM: Artificial sequence
<220> FEATURE:
<223> OTHER INFORMATION: Synthetic sequence: Reverse primer

<400> SEQUENCE: 20
agtgggtaat gcgcttggat                                            20

<210> SEQ ID NO 21
<211> LENGTH: 18
<212> TYPE: DNA
<213> ORGANISM: Artificial sequence
<220> FEATURE:
<223> OTHER INFORMATION: Synthetic sequence: Probe
<220> FEATURE:
<221> NAME/KEY: misc_feature
<222> LOCATION: 3, 6, 8, 10, 12, 13, 16
<223> OTHER INFORMATION: LNA base

<400> SEQUENCE: 21
caagacacaa acatgacc                                              18
```

TREATMENT OF BONE FRACTURE

FIELD OF THE INVENTION

The present invention relates to the use of mesenchymal stem cells obtained by culture of cells in the presence of HS-2 in the treatment of bone fracture.

BACKGROUND TO THE INVENTION

The drive to develop bone regenerative therapies to circumvent delayed and non-union of bone fractures is an important therapeutic issue, especially considering the millions of fractures which occur annually, at least 10% of which are unable to heal by themselves.

Heparan Sulphate 2 (HS-2) was identified and described in Brickman et al. (1998), J. Biol. Chem. 273(8), 4350-4359) and was purified from embryonic day 10 (E10) murine neuroepithelia. HS-2 was subsequently found to promote the growth of stem cells in ex vivo culture, while preserving their multipotentiality (WO2006/085209 A1 and US 2009/0148420 A1).

Mesenchymal stem cells (MSCs) are multipotent stem cells capable of differentiation into connective tissue and/or bone cells such as chondrocytes, osteoblasts, myocytes and adipocytes.

SUMMARY OF THE INVENTION

The inventors have discovered that mesenchymal stem cells obtained by culture of cells in the presence of HS-2 (HS-2 MSCs) are superior at bone growth and regeneration compared to MSCs obtained by culture in control conditions. Accordingly, the use of HS-2 MSCs in the repair of bone fracture is provided. In particular, fracture repair is enhanced when HS-2 MSCs are used compared to use of MSCs obtained by culture in control conditions. This enhancement comprises improvement in the speed of fracture repair relative to the speed of fracture repair obtained through treatment with MSCs obtained by culture in control conditions. Treatment of bone fracture using HS-2 MSCs leads to faster fracture repair, which may include faster bone growth, i.e. increased rate of new bone growth, faster bone matrix deposition, e.g. an increase in the rate of mineralisation, and/or an increase in the rate at which new bone volume is achieved in the fracture repair. These effects provide for a reduction in the time required to heal the fracture.

As such, in some aspects of the present invention HS-2 MSCs are provided for use in methods of improving the speed of bone fracture repair as compared to treatment without MSCs and/or with MSCs cultured under control conditions.

Embodiments of the invention are concerned particularly with the field of bone fracture repair through the use of MSCs to treat the fracture. Advantages of the present invention include the unexpected enhancement of bone fracture repair, demonstrated by improved speed of fracture repair, afforded by the use of a particular class of MSCs, namely HS-2 MSCs.

In one aspect of the present invention the use of mesenchymal stem cells obtained by culture of cells in the presence of HS-2 in the manufacture of a medicament for the treatment of bone fracture is provided.

In some embodiments the medicament is for use in a method of enhanced mesenchymal stem cell mediated fracture repair. The enhanced mesenchymal stem cell mediated fracture repair may comprise improvement in the speed of fracture repair relative to the speed of fracture repair obtained through treatment with mesenchymal stem cells obtained by culture in the absence of HS-2.

In another aspect of the present invention mesenchymal stem cells obtained by culture in the presence of HS-2 are provided for use in a method of treatment of bone fracture.

In a further aspect of the present invention a pharmaceutical composition is provided comprising mesenchymal stem cells obtained by culture in the presence of HS-2, wherein the pharmaceutical composition is for use in a method of treatment of bone fracture.

In some embodiments the mesenchymal stem cells or pharmaceutical composition are/is for use in a method of treatment comprising enhanced mesenchymal stem cell mediated fracture repair. The enhanced mesenchymal stem cell mediated fracture repair may comprise improvement in the speed of fracture repair relative to the speed of fracture repair obtained through treatment with mesenchymal stem cells obtained by culture in the absence of HS-2.

In another aspect of the present invention a biocompatible implant or prosthesis comprising a biomaterial and mesenchymal stem cells obtained by culture in the presence of HS-2 is provided.

In some embodiments the implant or prosthesis is coated with mesenchymal stem cells obtained by culture in the presence of HS-2. In some embodiments the implant or prosthesis is impregnated with mesenchymal stem cells obtained by culture in the presence of HS-2.

In a further aspect of the present invention a method of forming a biocompatible implant or prosthesis is provided, the method comprising the step of coating or impregnating a biomaterial with mesenchymal stem cells obtained by culture in the presence of HS-2.

In another aspect of the present invention a method of treating bone fracture in a subject is provided, the method comprising administration to the subject of a therapeutically effective amount of mesenchymal stem cells obtained by culture in the presence of HS-2.

In some embodiments the method is a method of enhanced mesenchymal stem cell mediated fracture repair, the method involving improvement in the speed of fracture repair relative to the speed of fracture repair obtained through treatment with mesenchymal stem cells obtained by culture in the absence of HS-2.

In some embodiments, prior to administration of mesenchymal stem cells, the method comprises culturing stem cells in contact with HS-2 so as to produce said therapeutically effective amount of mesenchymal stem cells.

In some embodiments the method further comprises the step of formulating said therapeutically effective amount of mesenchymal stem cells as a pharmaceutical composition comprising mesenchymal stem cells obtained by culture in the presence of HS-2 and a pharmaceutically acceptable carrier, adjuvant or diluent, wherein the pharmaceutical composition is administered to the subject.

In some embodiments the method comprises administering the mesenchymal stem cells or pharmaceutical composition to tissue surrounding the fracture.

In some embodiments administration of the mesenchymal stem cells or pharmaceutical composition comprises injecting the mesenchymal stem cells or pharmaceutical composition into tissue surrounding the fracture.

In a further aspect of the present invention a method of treating bone fracture in a subject is provided, the method comprising surgically implanting a biocompatible implant or prosthesis into tissue of the subject at or surrounding the site of fracture, which implant or prosthesis comprises a biomaterial and mesenchymal stem cells obtained by culture in the presence of HS-2.

In some embodiments the implant or prosthesis is coated with mesenchymal stem cells obtained by culture in the presence of HS-2. In some embodiments the implant or prosthesis is impregnated with mesenchymal stem cells obtained by culture in the presence of HS-2.

Description Of Preferred Embodiments

HS-2 MSCs

The present invention is concerned with the therapeutic treatment of bone fracture using HS-2 MSCs. In this specification "HS-2 MSCs" are mesenchymal stem cells obtained by, and obtainable by, culture of cells in the presence of HS-2.

Methods for obtaining HS-2 MSCs are described in WO2006/085209 A1 and US 2009/0148420 A1. The entire contents of each of these documents is incorporated herein by reference. As described there, mesenchymal stem cells obtained by culture of cells in the presence of HS-2 have been shown to have superior stem cell properties, as compared to mesenchymal stem cells obtained by culture of cells in the absence of HS-2, for example as obtained by culture in control conditions.

In some embodiments the step of obtaining HS-2 MSCs by culturing cells in the presence of HS-2 forms part of the invention.

In some preferred embodiments, the HS-2 MSCs are Human bone marrow cell line: hMSC-HS2 deposited by Agency for Science, Technology and Research A*Star VNSC Laboratory, Institute of Medical Biology, 8A Biomedical Drive, #0606 Immunos, Singapore, SG 138648 on 28 Dec. 2009 at The American Type Culture Collection (ATCC) under accession number PTA-10552 in accordance with the provisions of the Budapest Treaty.

In some embodiments of the present invention the HS-2 MSCs used to treat bone fracture may exclude HS-2, or only include trace amounts of HS-2.

HS-2 MSCs are a unique class of MSCs characterised by a unique combination of structural and functional properties that arise as a result of culturing the cells in the presence of HS-2.

In particular, MSCs from HS-2 culture show a significant retention of stem cell properties compared to stem cells cultured in the absence of HS-2 for the same period of time or for the same number of population doublings (PD). These stem cell properties may include longer telomere length, continued high level expression of molecular markers such as CD49a, CD73, CD105, CD90 and STRO-1 and maintenance of the multipotent properties of the stem cell, e.g. the ability to differentiate and form new tissue, and continued ability to minimise or avoid the host immune response.

MSCs obtained from culture in HS-2 have a unique genetic signature that is distinct from control cultures and can be objectively tested by analysis of gene expression and singular value decomposition. MSCs cultured in HS-2 show a much "younger" genetic signature compared to stem cells cultured in control culture (without HS-2) for the same length of time, i.e. the gene expression profile of MSCs cultured in HS-2 reflects that of cells grown in control cultures for a shorter period of time. This is consistent with the maintenance of stem cell multipotency when cultured in HS-2 and the loss of multipotency and other stem cell characteristics in MSCs cultured in the absence of HS-2. Accordingly, MSCs cultured in HS-2 represent a unique group of MSCs that are structurally distinguished from MSCs cultured in the absence of HS-2.

As described above, HS-2 has been shown to significantly increase the proliferation of a subpopulation of multipotent MSCs that have significantly longer telomeres and a greater expression of cell surface antigens that are characteristic of MSCs.

Structurally, HS-2 MSCs have significantly longer telomeres and a unique gene expression signature (as measured by Singular Value Decomposition (SVD) of Stem Cell Array Data—see WO2006/085209 A1 and US 2009/0148420 A1) compared to MSCs cultured in control conditions.

Average telomere length of MSCs expanded in the presence of HS-2 for 15 population doublings (PDs) is significantly longer than in MSCs expanded for 15 PDs in control media.

After long-term expansion in culture (45 days), HS-2 MSCs have a gene expression signature resembling that of control cells from much earlier passages indicating that HS-2 maintains the "sternness" of culture-expanded MSCs.

After 38 and 45 days expansion of MSCs in HS-2, expression of surface marker antigens STRO-1, CD49a, and CD105 was increased, and expression of CD73 unaffected Gene expression signature analysis (SVD analysis) also indicated that the structural effects of HS-2 on MSCs are not donor-specific and that gene expression signatures produced by SVD can be used to reliably compare cells from different donors.

Functionally, HS-2 MSCs are more multipotent than MSCs expanded in control culture, and have a longer life span in vivo, with no detectable telomerase activity.

HS-2 MSCs have also been found to maintain their proportions of CFU-F, (colony forming unit-fibroblastic), despite undergoing additional population doublings as compared to control cultures over the same culture period and thereby yielding an up to 8-fold increase in available CFU-F.

MSCs cultured in the presence of HS-2 for 13 or 21 PDs were found to have a frequency of CFU-F of 7% with the cloning assay from carry-on cultures of MSCs being comparable to previously reported frequencies obtained by enrichment of MSCs after STRO-1 sorting, where such sorting results in CFU-F frequencies below 1%, whereas the STRO-$1^{bright}$ population yields a frequency of 9%.

HS-2 MSCs may express one or more of CD49a, CD73, CD105, CD90, STRO-1 and may optionally not express CD45. Preferably, HS-2 MSCs are STRO-$1^{+bright}$. HS-2 MSCs have been found to exhibit a stable karyotype.

In accordance with the above it is clear that by obtaining MSCs through culture of cells in the presence of HS-2, the cells obtained (HS-2 MSCs) have unique structural and functional characteristics and represent a defined class of MSCs. The present invention concerns a specific use of HS-2 MSCs, namely in the treatment of bone fracture.

HS-2 MSCs may be further defined by reference to the duration of cell culture in the presence of HS-2 or the degree or rate of expansion of MSCs during culture in the presence of HS-2.

Duration of cell culture may be represented by the time for which the cells are cultured (e.g. a minimum number of days) or the number of population doublings (PDs) which the cells go through during the culture.

Accordingly, in some embodiments HS-2 MSCs are obtained by culture of cells in the presence of HS-2 for one of at least 5 days, at least 6 days, at least 7 days, at least 8 days, at least 9 days, at least 10 days, at least 12 days, at least 14 days, at least 16 days, at least 18 days, at least 20 days, at least 22 days, at least 24 days, at least 26 days, at least 28 days, at least 30 days, at least 32 days, at least 34 days, at least 36 days, at least 38 days, at least 40 days, at least 42 days, at least 44 days, at least 46 days, at least 48 days, at least 50 days, at least 60 days, at least 70 days, at least 80 days, at least 90 days, or at least 100 days. In some embodiments the HS-2 MSCs are obtained by culture in the presence of HS-2 for less than one of 100 days, 90 days, 80 days, 70 days, 60 days, or 50 days. Culture in the presence of HS-2 may be for a maximum of any one of 7, 9, 11, 13, 15, 20, 25, 30, 35, 40, 45, 50 or more days.

In some embodiments HS-2 MSCs are obtained by culture of cells in the presence of HS-2 through at least 5 PDs, at least 6 PDs, at least 7 PDs, at least 8 PDs, at least 9 PDs, at least 10 PDs, at least 12 PDs, at least 14 PDs, at least 16 PDs, at least 18 PDs, at least 20 PDs, at least 22 PDs, at least 24 PDs, at least 26 PDs, at least 28 PDs, at least 30 PDs, at least 32 PDs, at least 34 PDs, at least 36 PDs, at least 38 PDs, at least 40 PDs, at least 42 PDs, at least 44 PDs, at least 46 PDs, at least 48 PDs, at least 50 PDs, at least 60 PDs, at least 70 PDs, at least 80 PDs, at least 90 PDs, or at least 100 PDs. In some embodiments the HS-2 MSCs are obtained by culture in the presence of HS-2 for less than one of 100 PDs, 90 PDs, 80 PDs, 70 PDs, 60 PDs, 50 PDs, 40 PDs, 30 PDs, or 20 PDs.

In some embodiments at least 3% of cells in the culture or composition are colony forming units (CFUs), more preferably one of at least 4%, 5%, 6%, 7%, 8%, 9% or 10%. This may be assessed at the end of the culture or after a number of days or population doublings chosen from the lists above. The percentage of CFUs provides a measure of the proportion of stem cells in a cell culture.

Expansion of MSCs refers to the increase in population of MSCs in a culture, achieved through cell division.

Expansion may be measured by a doubling in the population of stem cells in the culture and the rate of population doubling may be used as a measure of the rate of stem cell expansion. In some embodiments HS-2 MSCs are obtained by culture of cells in the presence of HS-2 such that the rate of population doubling is in the range of one of about 0.5 PD/per day to about 1.2 PD/day, about 0.6 to about 0.9 PD/day, or about 0.6 to 0.8 PD/day. Between days 1 and 10 following addition of HS-2 to the culture media the rate of population doubling may be between about 0.6 and about 0.8 PD/day.

In some embodiments HS-2 MSCs are obtained by culture of cells in the presence of HS-2 for sufficient time to expand a single MSC to a population of more than $1 \times 10^3$ stem cells. The culture may initially contain more than one MSC. In that situation the total expanded MSC population is equivalent to the expansion of many MSCs by more than $1 \times 10^3$. The degree of expansion may more preferably be one of: $5 \times 10^3$, $1 \times 10^4$, $5 \times 10^4$, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$ or $5 \times 10^9$. The culture time to expand the MSCs may be between 5 and 50 days, more preferably between 10 and 45 days and more preferably less than one of 45 days, 40 days, 35 days, 30 days, 25 days, 20 days or 15 days.

In some embodiments HS-2 MSCs are obtained by culture of cells in the presence of HS-2 for sufficient time to expand a culture of MSCs from an initial culture size of at least about 2000 cells per $cm^2$ of culture space (e.g. of the culture dish or plastic) to an expanded culture size that contains at least $1 \times 10^3$ times more MSCs (i.e. at least about $2 \times 10^6$ MSCs). The initial culture size may be one of at least about 3,000 cells per $cm^2$, about 3500 cells per $cm^2$, at least about 4000 cells per $cm^2$, about 4500 cells per $cm^2$, 5000 cells per $cm^2$ and the expanded culture size may be one of at least about $3 \times 10^6$ cells per $cm^2$, about $3.5 \times 10^6$ cells per $cm^2$, at least about $4 \times 10^6$ cells per $cm^2$, about $4.5 \times 10^6$ cells per $cm^2$, $5 \times 10^6$ cells per $cm^2$. The initial culture may have less than one of: 6000, 5000, 4000, 3000 or 2000 cells per $cm^2$. The expanded culture may have more than one of: $5 \times 10^3$, $1 \times 10^4$, $5 \times 10^4$, $1 \times 10^5$, $5 \times 10^6$, $1 \times 10^6$, $5 \times 10^6$, $1 \times 10^7$, $5 \times 10^7$, $1 \times 10^8$, $5 \times 10^8$, $1 \times 10^9$ or $5 \times 10^9$ MSCs.

The culture time to expand between the initial culture size and the expanded culture size is preferably between about 10 and 50 days, more preferably between about 15 and 30 days. It may be less than one of 50, 45, 40, 35, 30, 25, 20 or 15 days. The methods described above may be applied to expand the MSC culture to an expanded culture size of $1 \times 10^4$, $1 \times 10^5$, $1 \times 10^6$, $1 \times 10^7$, $1 \times 10^8$, $1 \times 10^9$ cells or greater.

In some embodiments HS-2 MSCs are obtained by culture of cells in the presence of HS-2 for sufficient time to expand a culture of MSCs from an initial number of MSCs to an expanded number of MSCs, wherein the expanded number is at least 100 times, preferably at least 1000 times, the initial number and wherein the time to expand the culture between the initial number and the expanded number is less than 30 days, more preferably less than one of 28, 26, 24, 22, 20, 18, 16, 15, 14, 13, 12, 11, 10, 9, 8, 7, 6 or 5 days.

Methods of cell culture in the presence of HS-2 may comprise culture of cells in the linear (logarithmic) growth phase only, in post-confluent growth only, or may comprise growth extending over both linear and post-confluent phases. Methods of cell culture in the presence of HS-2 may also comprise passaging of cells. Culture of cells in the presence of HS-2 is preferably conducted at physiological temperatures.

In some embodiments cells used for cell culture may comprise cells capable of giving rise to MSCs, for example pluripotent or multipotent stem cells such as embryonic stem cells or induced pluripotent stem cells. In other embodiments cells used for cell culture may comprise mesenchymal stem cells. Cultures may also comprise other cells, e.g. non-stem cells associated with the stem cells in the tissue from which the stem cells are collected, and/or supporting cells, e.g. feeder cells. Cells used to initiate a culture of stem cells will preferably contain a high proportion of the respective stem cells, e.g. at least 60% stem cells, more preferably one of at least 70% stem cells, 80% stem cells, 90% stem cells, 95% stem cells, 96% stem cells, 97% stem cells, 98% stem cells, 99% stem cells or 100% stem cells. Cells, e.g. cells collected from previous cell culture or from live animals or humans, may be enriched prior to initiating cell culture, e.g. by enriching for markers such as STRO-1 or STRO-1$^{bright}$. Marker enrichment may be performed by cell sorting, e.g. FACS.

HS-2 MSCs described herein and the cells cultured in the presence of HS-2 in order to obtain HS-2 MSCs may be cells from any type of animal. Preferably they are mammalian. In some embodiments they are human. In other embodiments they are from a non-human mammal. The non-human mammal may be a domestic pet, or animal kept for commercial purposes, e.g. a race horse, or farming livestock such as pigs, sheep or cattle. Non-human mammals include rabbits, guinea pigs, rats, mice or other rodents (including any animal in the order Rodentia), cats, dogs, pigs, sheep, goats, cattle (including cows, e.g. dairy cows, or any animal in the order Bos), horse (including any animal in the order Equidae), donkey, and non-human primates.

Cells cultured in the presence of HS-2 in order to obtain HS-2 MSCs do not, initially, have to be MSCs. They may be multipotent or pluripotent stem cells induced to differentiate into MSCs during the culture.

The culture methodology described above is preferably performed in vitro. The term "in vitro" is intended to encompass experiments with cells in culture whereas the term "in vivo" is intended to encompass experiments with intact multicellular organisms.

In some embodiments a pharmaceutical composition comprising HS-2 MSCs generated by any of the methods described is provided. The pharmaceutical composition is useful in a method of medical treatment. Suitable pharmaceutical compositions may further comprise a pharmaceutically acceptable carrier, adjuvant or diluent. The pharmaceutical composition may comprise a scaffold or matrix material having cells implanted or adsorbed to the material. Such a composition may provide the basis of an implantable device or prosthesis, which may be surgically implanted into a patient in need of treatment.

In the present specification, culture of cells in the presence of HS-2 refers to culture of cells under conditions in which the cells being cultured are able to come into contact with HS-2. In preferred embodiments this comprises culturing cells in culture media containing HS-2. The culture media may be fluid, e.g. liquid or gel, and may contain HS-2 in addition to the normal nutrients, growth factors and matrix material. HS-2 will preferably be present in non-trace amounts. For example, the concentration of HS-2 in the culture media may range between about 1.0 ng/ml culture media to about 1000 ng/ml culture media. More preferably, the concentration of HS-2 in the culture media may be between about 5 ng/ml culture media and 200 ng/ml culture media, or between about 20 ng/ml culture media and 170 ng/ml culture media.

The properties of cells obtained from culture in the presence of HS-2 may be compared against cells of the same type obtained from culture in control conditions. "Control conditions" or "control culture" refers to culture of the cells under conditions in which the cells being cultured do not come into contact with HS-2 (preferably non-trace amounts of HS-2). As such, control conditions may comprise culture in culture media that contains the normal nutrients, growth factors and matrix material but no HS-2. Examples of control culture media for culture of MSCs include serum free media such as MesenCult®-ACF Medium (STEMCELL Technologies, Vancouver, Canada) or basal media such as MesenCult® MSC Basal Medium for Human Mesenchymal Stem Cells (STEMCELL Technologies, Vancouver, Canada).

Exemplary maintenance media for cell culture may comprise DMEM, 1,000 mg/l glucose supplemented with 10% fetal bovine serum (FBS) with 0.1% penicillin/streptomycin and 2 mM L-glutamine at 37° C. in a humidified 5% $CO_2$ incubator. Media may be changed at three-day intervals and the cells subcultured every 4-5 days (~80% confluency).

Bone Fracture

The present invention is concerned with the therapeutic use (human and veterinary) of HS-2 MSCs to treat bone fracture. HS-2 MSCs are reported here to augment wound healing in bone. HS-2 MSCs stimulate bone regeneration following injury and contribute to improved wound healing in bone. HS-2 MSCs provide improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS-2 MSCs include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bone fracture also includes pathological porosity, such as that exhibited by subjects with osteoporosis.

HS-2 MSCs and pharmaceutical compositions and medicaments comprising HS-2 MSCs are provided for use in a method of treatment of bone fracture in a mammalian subject.

Treatment may comprise wound healing in bone. The treatment may involve repair, regeneration and growth of bone. HS-2 MSCs facilitate fracture repair by facilitating new bone growth. HS-2 MSCs act to improve the speed of fracture repair enabling bone healing to occur faster leading to improved recovery time from injury. Treatment may lead to improved bone strength.

Treatment may also include treatment of osteoporosis or osteoarthritis.

Administration of HS-2 MSCs is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and Pharmaceutical Compositions

Medicaments and pharmaceutical compositions according to the present invention may be formulated for administration by a number of routes. HS-2 MSCs may be formulated in fluid or liquid form for injection, or as part of a gel suitable for application to bone or other tissue surrounding the fracture.

Administration is preferably in a "therapeutically effective amount", this being sufficient to improve healing of the bone fracture compared to a corresponding untreated fracture or to a fracture treated with MSCs obtained from culture in control conditions. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS-2 MSC doses may be administered in accordance with the guidance of the prescribing medical practitioner. Purely by way of example, HS-2 MSCs may be delivered in dosages of about $75 \times 10^6$ to about $100 \times 10^6$ cells, for example one of at least $50 \times 10^6$ cells, at least $60 \times 10^6$ cells, and at least $70 \times 10^6$ cells. Examples of the techniques and protocols mentioned above can be found in Remington's Pharmaceutical Sciences, 20th Edition, 2000, pub. Lippincott, Williams & Wilkins.

HS-2 MSCs may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS-2 MSCs may be administered directly to (e.g. applied to) the fracture during the surgical procedure.

Pharmaceutical compositions and medicaments of the invention may take the form of a biomaterial that is coated and/or impregnated with HS-2 MSCs. An implant or prosthesis may be formed from the biomaterial. Such implants or prostheses may be surgically implanted to assist in bone growth, regeneration, restructuring and/or re-modelling.

HS-2 MSCs may be applied to implants or prostheses to accelerate new bone formation at a desired location. The biomaterial may be coated or impregnated with HS-2 MSCs. Impregnation may comprise contacting the HS-2 MSCs with the biomaterial such that they are allowed to be adsorbed and/or absorbed onto and/or into the biomaterial. Coating may comprise adsorbing the HS-2 MSCs onto the surface of the biomaterial. Coating or impregnation of the biomaterial may involve seeding HS-2 MSCs onto or into the biomaterial.

The biomaterial should allow the coated or impregnated HS-2 MSCs to be released from the biomaterial when administered to or implanted in the subject. Biomaterial release kinetics may be altered by altering the structure, e.g. porosity, of the biomaterial.

In addition to coating or impregnating a biomaterial with HS-2 MSCs, one or more biologically active molecules may be impregnated or coated on the biomaterial. For example, at least one chosen from the group consisting of: HS-2, BMP-2, BMP-4, OP-1, FGF-1, FGF-2, TGF-β1, TGF-β2, TGF-β3; VEGF; collagen; laminin: fibronectin; vitronectin. In addition or alternatively to the above bioactive molecules, one or more bisphosphonates may be impregnated or coated onto the biomaterial along with HS-2 MSCs. Examples of useful bisphosphonates may include at least one chosen from the group consisting of: etidronate; clodronate; alendronate; pamidronate; risedronate; zoledronate. Optionally, HS-2 is excluded from being impregnated or coated on the biomaterial.

Biomaterials coated or impregnated with HS-2 MSCs may be useful in both medical and veterinary purposes. It will be appreciated that the present invention may improve the quality of life of a patient or potentially extend the life of an animal, for example a valuable race horse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L -lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019, 087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices.* 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications.* 2000; 14(3); 229-242; DeBlois Cote M F. Doillon C J. Heparin-fibroblast growth factor fibrin complex: in vitro and in vivo applications to collagen based materials. *Biomaterials.* 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

The biomaterial can be supplemented with additional cells. For example, one can "seed" the biomaterial (or co-synthesise it) with fibroblast derived feeder cells, which may be useful for supporting growth and maintenance of the HS-2 MSCs.

The subject to be treated may be any animal or human. The subject is preferably mammalian. In some embodiments the subject is a human. In other embodiments the subject is an animal, more preferably a non-human mammal. The non-human mammal may be a domestic pet, or animal kept for commercial purposes, e.g. a race horse, or farming livestock such as pigs, sheep or cattle. As such the invention may have veterinary applications. Non-human mammals include rabbits, guinea pigs, rats, mice or other rodents (including any animal in the order Rodentia), cats, dogs, pigs, sheep, goats, cattle (including cows or any animal in the order Bos), horse (including any animal in the order Equidae), donkey, and non-human primates. The subject may be male or female. The subject may be a patient.

Heparan Sulphate and HS-2

Heparan sulfate proteoglycans (HSPGs) represent a highly diverse subgroup of proteoglycans and are composed of heparan sulfate glycosaminoglycan side chains covalently attached to a protein backbone. The core protein can exist in three forms: a secreted form known as perlecan, a form anchored in the plasma membrane known as glypican, and a transmembrane form known as syndecan. They are ubiquitous constituents of mammalian cell surfaces and most extracellular matrices.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O—, 6-O— and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1->4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, *J. Biol. Chem.* 273, 24979; Sugahara and Kitagawa, 2000, *Curr. Opin. Struct. Biol.* 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), *J. Biol. Chem.* 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, *Glycobiology* 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 μl of 0.5 M $H_2SO_4$ and 0.5 M $Ba(NO_2)_2$ separately on ice for 15 min. After cooling, the Ba(NO$_2$)$_2$ is combined with the H$_2$SO$_4$ and vortexed before being centrifuged to remove the barium sulphate precipitate. 125 μl of HNO$_2$ was added to GAG samples resuspended in 20 μl of H$_2$O, and vortexed before being incubated for 15 min at 25° C. with occasional mixing. After incubation, 1 M Na$_2$CO$_3$ was added to the sample to bring it to pH 6. Next, 100 μl of 0.25 M NaBH$_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM CaCl$_2$ at pH 7.5. Purely by way of example, Heparinase III may be added at 5 mU per 1 μg of HS and incubated at 37° C. for 16 h before stopping the reaction by heating to 70° C. for 5 min.

Di- and tetrasaccharides may be eluted by column chromatography.

The heparan sulfate used in the present invention to obtain HS-2 MSCs is heparan sulfate 2 (HS-2). HS-2 denominates the sugar chains of an HSPG, which have been found to have affinity for FGF-2. HS-2 has a molecular weight of approximately 25 kDa and thus, assuming an average molecular mass of 400 Da per disaccharide, consists of about 60 disaccharides. The disaccharide composition of HS-2 is set forth in Brickman et al. (Glycobiology Vo. 8 No. 5 pp. 463-471, 1998), which is herein incorporated by reference in its entirety.

By "heparan sulfate 2" or "HS-2" is meant the heparan sulfate that is described by Brickman et al. (1998), J. Biol. Chem. 273(8), 4350-4359) and that is derived (and obtainable) from embryonic neuroepithelium, preferably mammalian embryonic neuroepithelium more preferably murine embryonic neuroepithelium, and is preferably capable of interacting with FGF-2. Accordingly, this heparan sulfate 2 is obtainable from heparan proteoglycans of murine cells at embryonic day 10 as described by Brickman (supra). The HS-2 that is used in the experimental section of the present application is derived from embryonic mouse, it has been found to be very potent on mouse, human, rat, chicken, *Xenopus* and *drosophila* cells. In line with these results a universal mechanism amongst any higher organism (for example insects or vertebrates such as mammals, birds, reptiles or fish) is contemplated here. Thus, any heparan sulfate 2 and any respective heparan sulfate proteoglycan that is capable of interacting with FGF-2 and that is able to promote or facilitate proliferation and/or maintenance of stem cells ex vivo (in vitro) is encompassed in the present invention, including such heparan sulfate proteoglycan and heparan sulfate 2 that is yet to be isolated from a specific species. The isolation and determination of the functionality of the isolated heparan sulfate or heparan sulfate proteoglycan is well within the knowledge of the person of ordinary skill in the art and can be carried out as described by Brickman et al. (1998), *J. Biol. Chem.* 273(8), 4350-4359, for example.

HS-2 can be obtained from embryonic day 10 (E10) mouse neuroepithelium. The molecular weight of HS-2 is shown in FIG. 9 following a variety of treatments including pronase treatment to remove any associated protein component, mild alkali and heparinase. HS-2 can be further characterised by analysis of the percentage of linkages sensitive to treatment with either low pH HNO$_2$, heparitinase or heparanase. The results are shown in FIG. 10. The disaccharide composition of HS-2 following nitrous acid digestion is shown in FIG. 11. The tetrasaccharide composition of HS-2 following nitrous acid digestion is shown in FIG. 12. The disaccharide composition of HS-2 following treatment with a mixture of heparin lyases is shown in FIG. 13. The sulfation characteristics of the disaccharides shown in FIG. 13 are shown in FIG. 14. Methodology for determining the percentage of linkages sensitive to susceptible treatment with either low pH HNO$_2$, heparitinase or heparanase; nitrous acid digestion and heparin lyase digestion are described elsewhere in this application.

In this specification reference to HS-2 includes HS obtained from embryonic day 10 (E10) mammalian neuroepithelium, preferably mouse. Reference to HS-2 may also include HS having substantially similar structure and/or function to HS-2 set forth in Brickman et al. in *Glycobiology Vol.* 8 No. 5 pp. 463-471, 1998. HS of substantial similarity to HS-2 of Brickman et al may include HS having:

(i) a molecular weight no more than 10%, more preferably 5%, greater or less than the molecular weight shown in FIG. 9 for the corresponding treatment; and/or (ii) a percentage of linkages susceptible to low pH nitrous acid, heparitinase or heparanase treatment that is no more than 10%, more preferably 5%, greater or less than the percentage shown in FIG. 10 for the corresponding treatment; and/or (iii) a nitrous acid digestion disaccharide composition wherein each disaccharide corresponding to those shown in FIG. 11 is present and the percentage composition of each disaccharide is no more than 20%, more preferably 15%, 10%, 5%, 3%, 2% or 1%, greater or less than the percentage composition shown in FIG. 11; and/or (iv) a nitrous acid digestion tetrasaccharide composition wherein each tetrasaccharide corresponding to those shown in FIG. 12 is present and the percentage composition of each tetrasaccharide is no more than 20%, more preferably no more than 15%, 10%, 5%, 3%, 2% or 1%, greater or less than the percentage composition shown in FIG. 12; and/or (v) a heparin lyase disaccharide composition wherein each disaccharide corresponding to those shown in FIG. 13 is present and the percentage composition of each disaccharide is no more than 20%, more preferably 15%, 10% or 5%, greater or less than the percentage composition shown in FIG. 13.

Stem Cells

The term "stem cell" generally refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Embryonic Stem (ESCs) cells may be isolated from the inner cell mass (ICM) of the blastocyst, which is the stage of embryonic development when implantation occurs.

Pluripotent stem cells are true stem cells, with the potential to make any differentiated cell in the body. However, they cannot contribute to making the extraembryonic membranes which are derived from the trophoblast. Several types of pluripotent stem cells have been found.

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

Adult stem cells comprise a wide variety of types including neuronal, skin and the blood forming stem cells which are the active component in bone marrow transplantation.

These latter stem cell types are also the principal feature of umbilical cord-derived stem cells. Adult stem cells can mature both in the laboratory and in the body into functional, more specialised cell types although the exact number of cell types is limited by the type of stem cell chosen.

Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007), Yu J, et al. (2007) and Takahashi et al., (2007), all of which are incorporated herein by reference.

iPS cells are typically derived by transfection of certain stem cell-associated genes into non-pluripotent cells, such as adult fibroblasts. Transfection is typically achieved through viral vectors, for example through retroviral reprogramming. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

IPSCs may be induced from somatic cells such as fibroblasts by transfection with one or more transcription factors. In some cases, cells are transformed with Oct3/4, Sox2, c-Myc and Klf4. The cells may be additionally transfected with other genes, including transcription factors and/or marker genes. The genes may be introduced using a transposon system such as the Cre/IoxP recombination system, or using non-integrating vectors in order to produce iPSCs free of exogenous reprogramming genes. Transfection may be achieved using viral vectors, such as a retrovirus. The virus may be an amphotropic virus. Once the cells have been transfected, they may be grown on feeder cells before transfer to an ESC culture medium.

iPS cells may be derived from any suitable cell type, including lung, foreskin fibroblasts, skin fibroblasts, keratinocytes, blood progenitor cells, bone marrow cells, hepatocytes, gastric epithelial cells, pancreatic cells, neural stem cells, B lymphocytes, ES derived somatic cells and embryonic fibroblasts. In some cases, the cells are not human dermal fibroblasts. The IPSCs may exhibit similar patterns of gene expression and phenotype to ESCs.

Sources of Induced Pluripotent Stem Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, Jul. 2007 ᵃ2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human tri embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4): 581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

Induced pluripotent stem cells have the advantage that they can be obtained by a method that does not cause the destruction of an embryo, more particularly by a method that does not cause the destruction of a human or mammalian embryo. As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Mesenchymal Stem Cells

Mesenchymal stem cells are known as being multipotent and exhibit the potential for differentiation into different cells/tissue lineages, including cartilage, bone, adipose tissue, tendon, and ligament. These multipotent mesenchymal progenitor cells are denoted as stromal or mesenchymal stem cells. Bone marrow contains two main cell types: hematopoietic cells and stromal cells. The stem cells for non hematopoietic tissues are referred as mesenchymal cells because of their ability to differentiate as mesenchymal or stromal cells.

Accordingly, in this specification mesenchymal stem cells (MSCs) refers to multipotent stem cells capable of differentiation into osteoblasts, chondrocytes, myocytes, adipocytes and endothelium. In this specification MSCs particularly refers to multipotent stem cells capable of differentiation into osteoblasts as part of the process of formation of bone.

Mesenchymal cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Suitable MSCs may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES *British Journal of Haematology* 121 (2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. *Stem Cells Dev.* 2009 Jul. 20 (Epub)).

Differentiation of MSCs to the osteogenic lineage may be achieved by culture in osteogenic medium. For example, MSCs are seeded at $3,000/cm^2$ in maintenance medium (DMEM, 1 g/l glucose, 10% FCS, 2 mM L-glutamine, 50 U/ml penicillin and 50 U/ml streptomycin) in 6-well, 12-well and chamber slides for 24 h before changing to osteogenic media (maintenance medium, 10 nM dexamethasone, 25 μg/ml ascorbic acid and 10 mM β-glycerophosphate). Cells are then maintained for up to 28 days with a media change every 3-4 days. After 14 days cells in the chamber slides may be fixed in 4% PFA and stored at 4° C. in PBS for immunohistochemistry. After 14 and 28 days the cells are stained with alizarin red S for calcium, and von Kossa for calcium phosphate. RNA may also be extracted for analysis using the Nucleospin RNA extraction kit according to the manufacturer's instructions (Macherey Nagel) and protein samples may be extracted for analysis.

Differentiation of MSCs to the adipogenic lineage may be achieved by culture in adipogenic medium. For example, MSCs are seeded at $18,000/cm^2$ in maintenance medium and incubated as above for 2 days. Media is removed and cells are washed once in PBS before the addition of adipogenic maintenance media (DMEM, 4.5 g/l glucose, 10% FCS, L-glutamine and penicillin and streptomycin) or adipogenic media (adipogenic maintenance media with 10 μg/ml insulin, 115 μg/ml methyl-isobutylxanthine, 1 μM dexamethasone and 20 μM indomethazine). Cells are then maintained for up to 28 days with a media change every 3-4 days. After 14 and 28 days the cells may be stained with oil-red-O to stain the lipid droplets. RNA and protein may also be extracted for analysis.

Differentiation of MSCs to the chondrogenic lineage may be achieved by culture in chrondrogenic medium. For example, MSCs are counted and resuspended at $5\times10^5$ cells/ml in chondrogenic media (DMEM with Cambrex chondrogenic single aliquots) with or without 10 ng/ml TGF☐3 (Cambrex) and then 500 ml aliquots were put into 15 ml tubes before centrifugation at 150×g at room temperature for 10 min and incubated at 37° C. for 2 days. After two days the tubes will contain loose round pellets. Pellets are maintained for 21 days with a media change every 3-4 days before RNA is isolated using Trizol (Invitrogen) or cell pellets are fixed in 4% PFA and embedded for cryosectioning. Serial sections are made before slides are stored at −80° C. for immunohistochemistry.

When osteogenic and adipogenic differentiation are investigated under confluent conditions, cells may be seeded at 30,000/cm$^2$ and allowed to reach confluence before switching to the relevant differentiation media and cultured as above.

Culture of Stem Cells

Any suitable method of culturing stem cells may be used, and any suitable container may be used to propagate stem cells. Suitable containers include those described in US Patent Publication US2007/0264713 (Terstegge).

Containers may include bioreactors and spinners, for example. A "bioreactor" is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 cm$^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

Methods of cell culture may comprise passaging, or splitting during culture. The methods may involve continuous or continual passage.

Cells in culture may be dissociated from the substrate or flask, and "split", subcultured or passaged, by dilution into tissue culture medium and replating/re-cultuting.

The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. Passages may be expressed as generations of cell growth. Stem cells may be propagated for 1, 2, 3, 4, 5, 6, 7, 8, 9, 10, 11, 12, 13, 14, 15, 16, 17, 18, 19, 20, 21, 22, 23, 24, 25 generations or more. Stem cells may be propagated for 1, 2, 3, 4, 5, 6, 7, 8, 9, 10, 11, 12, 13, 14, 15, 16, 17, 18, 19, 20, 21, 22, 23, 24, 25 cell doublings or more Co-Culture and Feeders Methods may comprise culturing stem cells in the presence or absence of co-culture. The term "co-culture" refers to a mixture of two or more different kinds of cells that are grown together. The two or more different kinds of cells may be grown on the same surfaces, such as particles or cell container surfaces, or on different surfaces. The different kinds of cells may be grown on different particles.

Feeder cells may mean cells which are used for or required for cultivation of cells of a different type. In the context of stem cell culture, feeder cells have the function of securing the survival, proliferation, and maintenance of cell pluripotency or multipotency. Cell pluripotency/multipotency may be ensured by directly co-cultivating the feeder cells. For example, the inner surface of the container such as a culture dish may be coated with a feeder cell layer. The feeder cells release nutrients into the culture medium. Alternatively, or in addition, the feeder cells may be cultured in a medium to condition it. The conditioned medium may be used to culture the stem cells. Thus, arrangements in which feeder cells are absent or not required are also possible.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 9. A summary of the estimated $M_r$ of extracellular-HS2 from E10 neuroepithelium. The source of HS was subjected to separation on a 1×120 cm Sepharose CL-6B column after a variety of treatments. The size of purified full length HS was determined both before and after mild alkali treatment to determine the presence of more than one chain per protein core. In addition, the approximate distance between heparinase-sensitive disaccharides was determined by isolating the non-resolved, large oligosaccharides from a Bio-Gel P-10 column and rerunning them on a Sepharose CL-6B column.

FIG. 10. Proportion of the linkages in HS-2 susceptible to low pH $HNO_2$, heparitinase and heparinase. Radiolabelled heparan sulphate 2 was treated with low pH $HNO_2$, heparinase, or heparitinase and fractioned on a Bio-Gel P-10 column. The percentage of the total treatment-sensitive linkages was determined in two separate experiments by $\Sigma A_n/n$ where $A_n$ is the percentage of total radioactivity in that peak, and n is the number of disaccharide repeat units in the oligosaccharides as determined by the elution position (Turnbull and Gallagher, 1990; Kato et al. 1994).

FIG. 11. Nitrous acid-derived disaccharide composition of heparan sulfate from E10 neuroepithelia. Radiolabelled HS-2 was depolymerized by deaminitive cleavage with low pH $HNO_2$. Disaccharides were isolated after $HNO_2$ treatment of the GAGs and the samples then run on a 1×120 cm Bio-Gel P-2 column. The resulting disaccharides were fractionated by SAX-HPLC. Areas under the peaks were integrated to give the disaccharide composition and subsequently, the percentage composition in each sample.

FIG. 12. Tetrasaccharides from $HNO_2$ treated HS-2 separated by SAX-HPLC. Tetrasaccharides derived from $HNO_2$ treated heparan sulfates were originally separated on a Bio-Gel P-2 column and were then further resolved on SAX-HPLC. The percentage of each was determined by calculating the radioactivity in each peak and comparing it to the total radioactivity in all peaks combined. Tetrasaccharide peak numbers in the left column correspond to the peaks from SAX-HPLC. The degree of sulfation was determined by comparison of these tritiated samples with peaks generated by dual $^{35}S/^3H$ radiolabelled samples (from Dr. Gordon Jayson, University of Manchester) run on the same column under identical conditions.

FIG. 13. Disaccharide composition of heparan sulfate from E10 neuroepithelium following heparin lyase treatment. Heparan sulfate 2 was completely depolymerized with a mixture of heparan lyases. The resulting unsaturated disaccharides were isolated on a P-2 column and fractionated by strong anion exchange column chromatography. The area under each resultant curve was integrated to calculate the percentage of each disaccharide in each sample. Numbers represent the average of two runs (for the primary GAG samples) and three runs (for the 2.3D derived samples). Over 97% disaccharides were recovered from each sample.

FIG. 14. Sulfation characteristics of disaccharides from the HS-2 pools shown in FIG. 13.

FIG. 18. HS-2 expands hMSCs that are able to clone and undergo multilineage differentiation. (A) Single cell colony formation of cells expanded in HS-2 or control media. Cloning frequency of cells expanded for 13 PDs in HS-2 or control media in 96-well plates. Error bars represent standard deviation, n=3. (B) Multilineage differentiation assay of representative clones from cultures expanded for 13 PDs in control or HS-2 media. From top to bottom: phase contrast micrographs of lipid containing cells from adipogenic cultures, alizarin red staining of mineralizing osteogenic cultures, H&E and alcian blue staining of chondrogenic cultures. (Scale bars=200 μm).

FIG. 23. The presence of FGF2 but not HS-2 decreases adipogenic differentiation of hMSCs. At confluence hMSCs were changed to maintenance (control; ▲) or adipogenic media with or without (Differentiation control; ●) supplementation with 160 ng/ml HS-2 (▼) or 10 ng/ml FGF2 (■). Cells were cultured for 32 days with a media change twice a week. (A) Phase contrast photomicrograph (×200 magnification) of cells in the four differentiation conditions. Cells in maintenance media with or without supplements failed to accumulate lipid. (B) Adiponectin ELISA at every media change. Samples were collected, stored at −80° C. and analyzed in triplicate using an Adiponectin ELISA kit (Otsuka pharmaceutical) following the instructions from the manufacturer. HS had no adverse effect on adiponectin levels, compared to FGF-2, which greatly inhibited its expression across all time points.

FIG. 24. Presence of FGF2 but not HS-2 decreases osteogenic differentiation of hMSCs. At confluence, media was changed to maintenance or osteogenic with or without (CTRL) supplementation with 160 ng/ml HS-2 or 10 ng/ml FGF2. Cells were cultured for 21 days with a media change twice a week. Cells cultured in osteogenic media supplemented with FGF2 lifted from the plate after 16 days. (A) Phase contrast photomicrograph (×200 magnification) of cells in the four differentiation conditions after 14 and 21 days. (B) hMSC mineralization after 14 and 21 days as determined by alizarin red staining. Cells in maintenance media failed to mineralize.

FIG. 25. Table of Taqman primer/probes used for quantitative PCR.

FIG. 28. Table listing genes identified by angle selection. Genes are sorted based on angles subtended by their loadings with respect to the origin and Euclidean distances greater than the 90-th percentile on the projection space defined by the 2 maximally-variant axes. Provided are Unigene Ids, Genbank RefSeq numbers, gene symbols and descriptions.

FIG. 29. Gene selection based on coefficients of singular vectors. Filtering of coefficients was based on a 90-th percentile of Euclidean distance from the origin (black cross). Clusters denote angles subtended by genes of each cluster with respect to the x-axis. They are colored blue (cluster 1), red (cluster 2) and green (cluster 3) and enclosed in ellipses. Genes are numbered as in FIG. 28.

FIG. 32. Table of bootstrap statistics. $^a$Euclidean distance estimates were based on first 2 singular vectors. $^b$Lower CL and $^c$Upper CL provide 95% confidence limits estimated within 1000 bootstrap replicates.

DETAILED DESCRIPTION OF THE INVENTION

Figure 1:
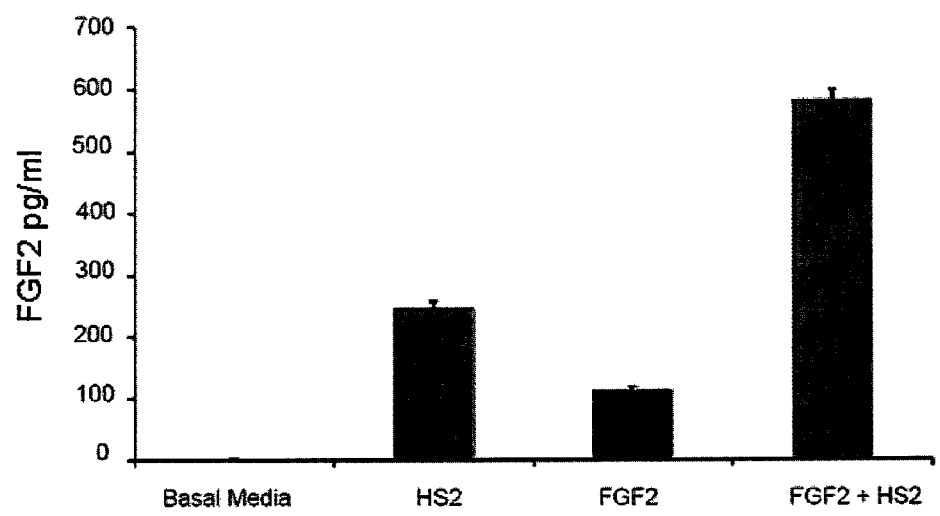
FIG. 1. HS-2 increases endogenous FGF2. Human MSCs (hMSCs) grown in HS-2 (160 ng/ml) produce endogenous FGF2 at higher levels than cells not given HS-2 (basal), as measured by FGF2 ELISA. Cells given FGF2 (5 ng/ml) also produce FGF2 but at lower levels compared to cells grown in HS-2. Cells given a combination of HS-2 and FGF2 make even more FGF2.
Figure 2A:
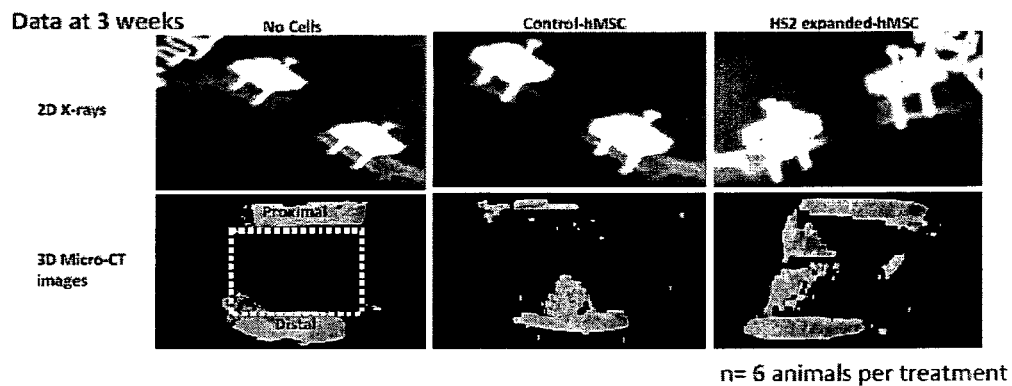
FIG. 2. HS-2 expanded human MSCs accelerate bone healing. (A) Micrographs showing 2D X-ray and 3D Micro-CT Images of bone regeneration at 3 weeks after fracture in animals given no cells, control-hMSC and HS-2 expanded-hMSC. (B) Chart showing percentage bone volume at the fracture site at 3 weeks after fracture in animals given no cells, control-hMSC and HS-2 expanded-hMSC.
Figure 2B:
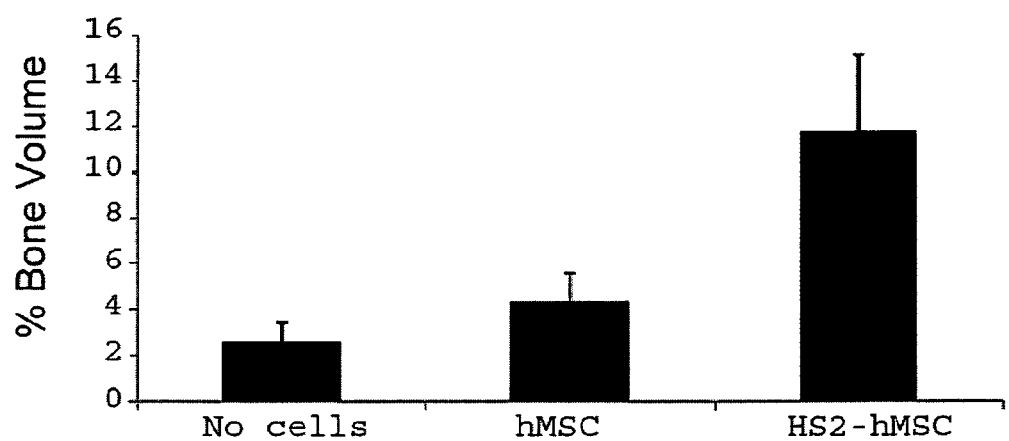
Figure 3A:
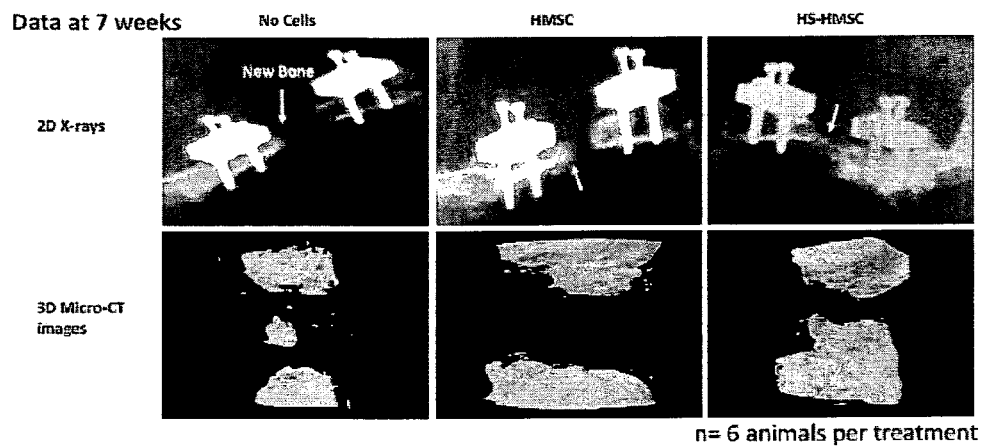
FIG. 3. HS-2 expanded human MSCs accelerate bone healing. (A) Micrographs showing 2D X-ray and 3D Micro-CT Images of bone regeneration at 7 weeks after fracture in animals given no cells, control-hMSC and HS-2 expanded-hMSC. (B) Chart showing percentage bone volume at the fracture site at 7 weeks after fracture in animals given no cells, control-hMSC and HS-2 expanded-hMSC.
Figure 3B:
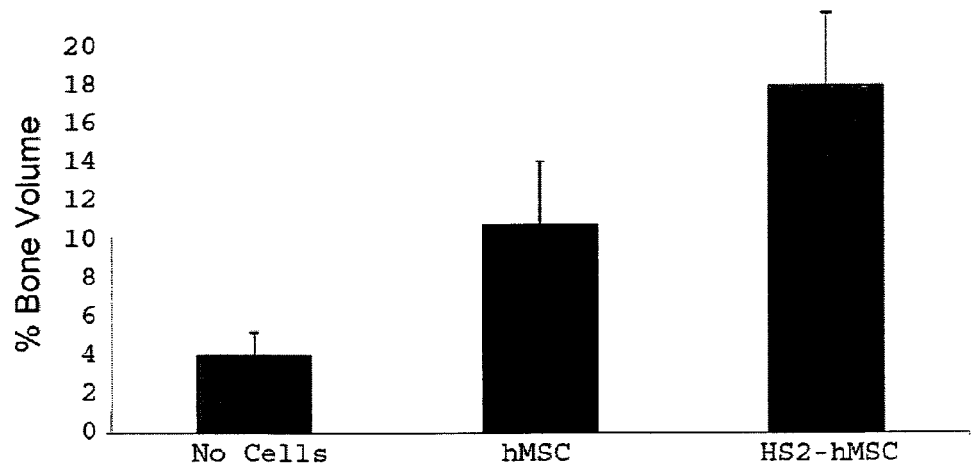
Figure 4:
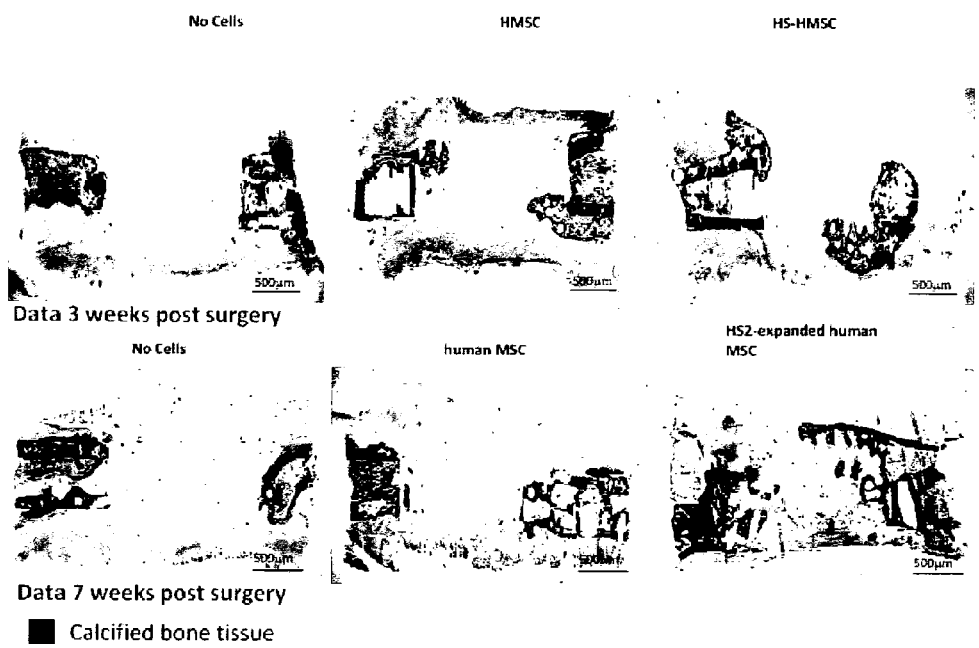
FIG. 4. von Kossa staining resin histology. Micrographs showing von Kossa staining at the fracture site at 3 and 7 weeks after fracture in animals given no cells, control-hMSC and HS-2 expanded-hMSC. Black staining (von Kossa positive) marks areas of calcified bone. Animals treated with HS-2 expanded cells have increased bone formation compared to control and non treated animals.
Figure 5:
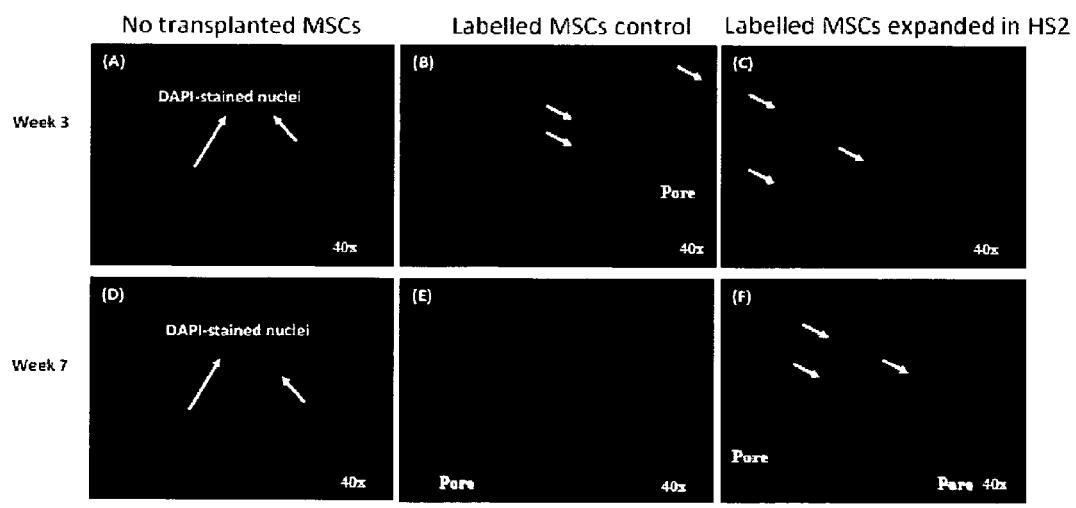
FIG. 5. Presence of red nanodots indicates that the transplanted HS-2 MSCs are surviving up to 7 weeks post transplantation whereas control MSCs can only be found at 3 weeks. Blue (DAPI) stains all the cells, both transplanted and host.
Figure 6:
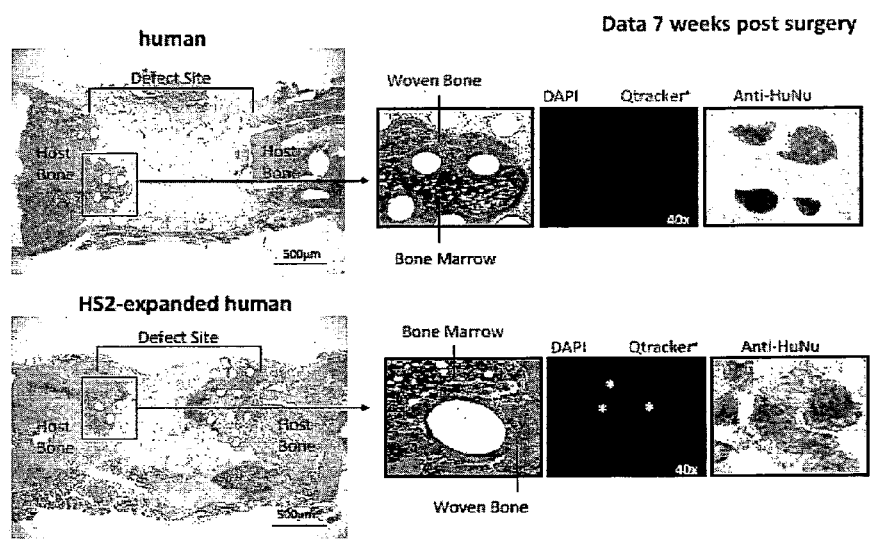
FIG. 6. Survival of HS2-expanded human MSCs. (Left Hand side) Representative histological sections of femurs at week 7 in control (top) or HS-2-treated animals (bottom). NB: New bone, BM: Bone marrow, SC: Scaffold, HC: Hypertrophic chondrocytes, P: Pores of scaffold and OB: Osteocalcin-positive osteoblasts. Brackets delineate the ends of the defect. (Right hand side) Representative DAPI-stained cryosections of femurs, to reveal surviving hMSCs in the defect. DAPI stains the nuclei of cells blue, while the hMSCs that were pre-labelled with QTracker®, fluoresce red. Anti-Human Nuclear Antigen antibodies were used to confirm the presence of implanted stem cells, which were especially prominent after HS-2 treatment.
Figure 7:
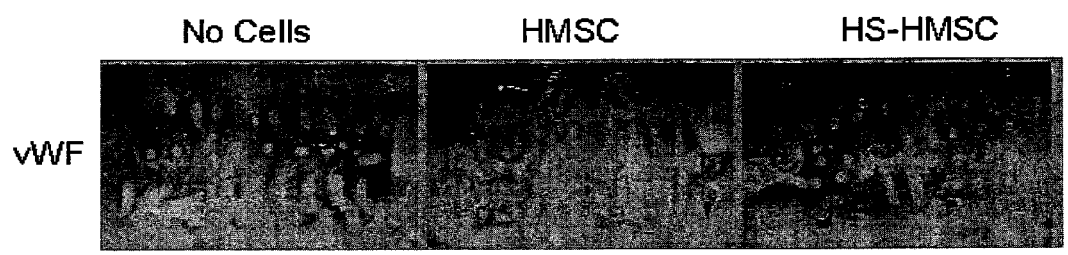
FIG. 7. Micrographs showing von Willebrand Factor (vWF) staining of blood vessels at 7 weeks post transplantation in animals given no cells, control-hMSC and HS-2 expanded-hMSC. Increased staining for vWF in HS-2 MSC treated fractures indicates that HS2-expanded hMSCs induce a greater degree of vascularization compared to control MSCs.
Figure 8A:
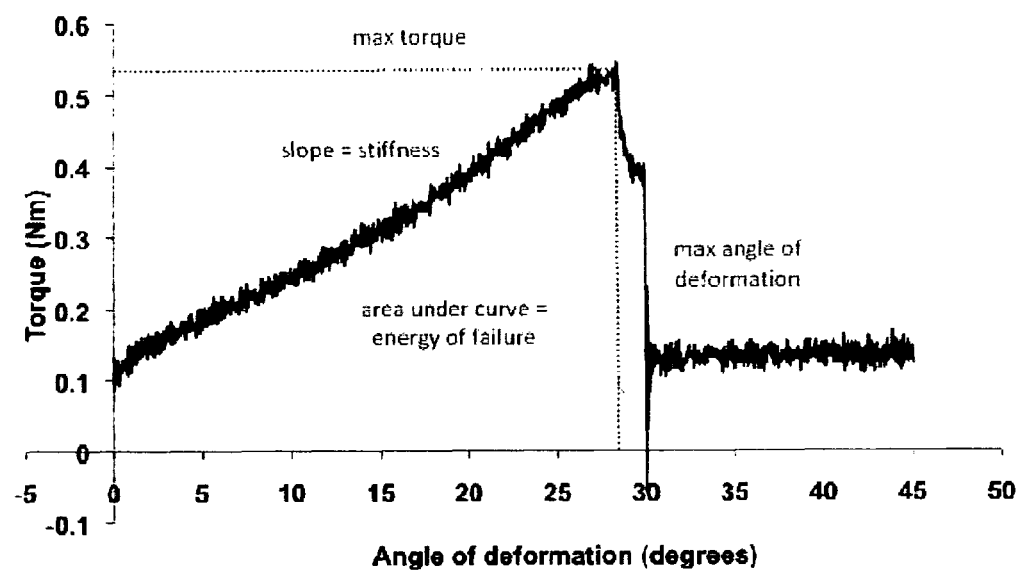
FIG. 8. Torsional biomechanics. (A) Chart illustrating torsional stiffness of a bone in general. (B) Torque strength of bone after fracture at 7 weeks post transplantation in animals given no cells, control-hMSC and HS-2 expanded-hMSC. Torque strength in animals given HS-2 MSCs is significantly greater than torque strength in animals given no cells or control-hMSC.
Figure 8B:
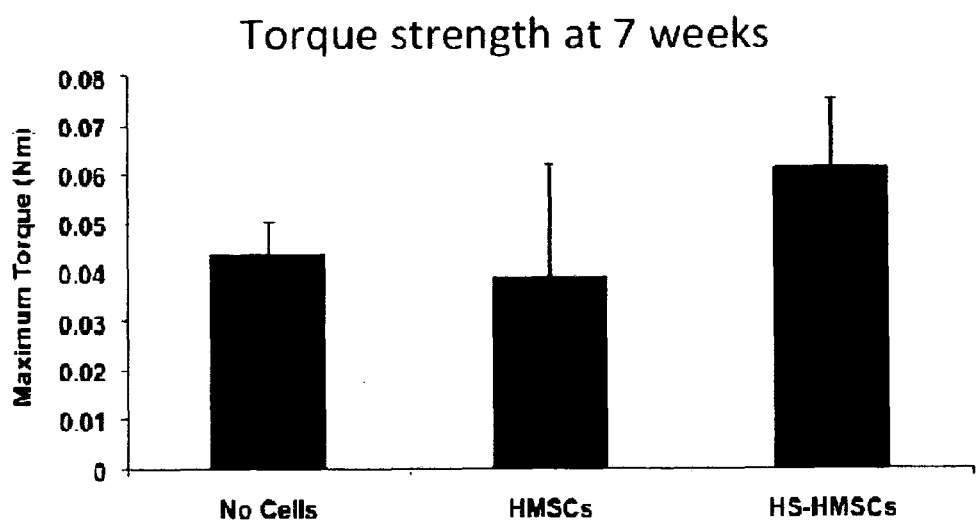

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLE 1

Methods
Human Msc Isolation and Cell Culture

Human mesenchymal stem cells (hMSCs) (PT-2501; Lonza) were maintained in DMEM, 1,000 mg/l glucose supplemented with 10% fetal bovine serum (FBS) with 0.1% penicillin/streptomycin and 2 mM L-glutamine at 37° C. in a humidified 5% $CO_2$ incubator. Media was changed at three-day intervals and the cells subcultured every 4-5 days (~80% confluency); aliquots from passages 2-5 were frozen in liquid nitrogen for future use. Unprocessed primary human bone marrow (#1M-125) from three healthy donors was purchased from Lonza and subjected to Ficoll gradient separation to isolate the hMSCs and to eliminate unwanted cell types. Cells were then plated and cultured as previously reported {Rider, 2008 #85}.

Characterization of hMSC Immunophenotype

Flow cytometric analysis was performed to compare profiles of HS-2-expanded and control-expanded hMSCs for CD49a, CD73 (BD Bioscience), CD105 (eBioscience) and STRO-1 (R&D Systems), or isotype-matched controls as previously reported {Rider, 2008 #85}. Samples were analyzed using a Guava PCA-96 bench top flow cytometer and Guava Express Software (Millipore).

Colony-Forming Units-Fibroblastic

Colony efficiency was assayed in the presence or absence of HS-2-supplement. Bone marrow mononuclear cells ($3 \times 10^5/cm^2$) or hMSCs (30 cells/cm$^2$) were plated in triplicate, in 24-well plates and cultured for 14 days as previously described {Rider, 2008 #85}. Colonies with more than 50 cells that were not in contact with other colonies were counted.

Proliferation and Apoptotic Assays

Cell number, cell cycle kinetics (propidium iodide) and apoptosis (Annexin V) were analyzed on a GUAVA PCA-96 benchtop flow cytometer following the manufacturer's instructions (Millipore). Proliferation-related metabolic activity was determined by incubation of cells with WST-1 as per the manufacturer's recommendations (Roche). Human MSCs ($3.3 \times 10^3$) were plated in 96-well plates in HS-2-supplemented or maintenance media and cultured for varying time points. For BrdU assays, cells ($2.1 \times 10^5$ cells/cm$^2$) were allowed to adhere (2 h) in 96-well plates, then serum-starved (0.2% FBS), before the addition of media with or without HS-2. BrdU incorporation was measured using the Cell Proliferation ELISA kit (Roche) following the manufacturer's instructions. To determine the effect of HS-2 supplementation on cumulative cell number (long-term growth), hMSCs were plated at $5 \times 10^3$ cells per cm$^2$ and cultured to 85% confluency, lifted with tryspin/EDTA, counted (Guava Express Software), and then replated at 5×10³ cells per cm². This process was repeated for 45 days with media changes twice weekly.

Telomere Length

Figure 22:
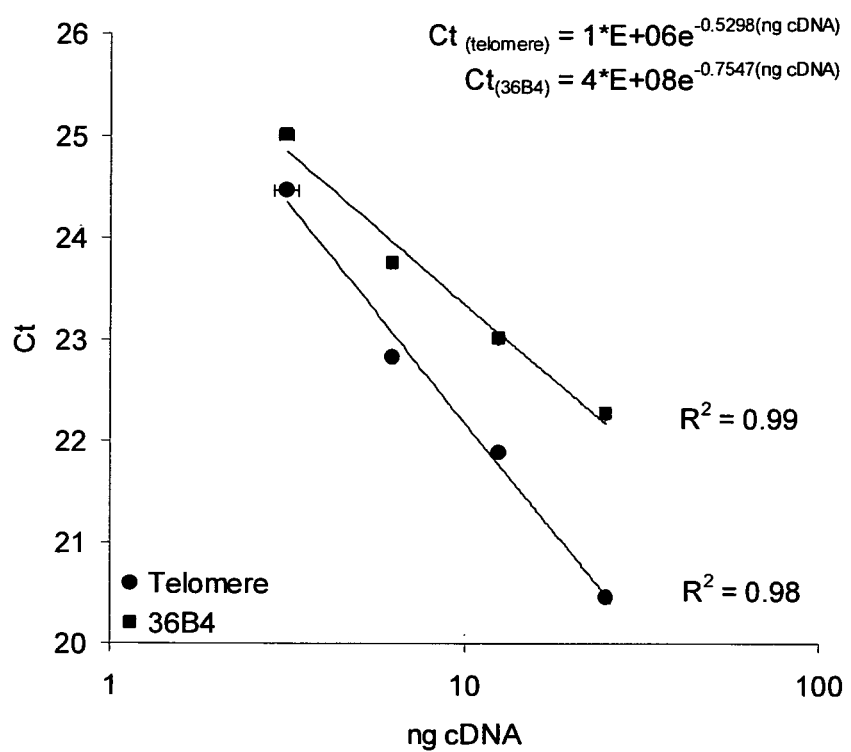
FIG. 22. Standard curve for relative quantification of telomere length in hMSCs. Chromosomal DNA from a confluent layer of human embryonic stem cell line BG01V (ATCC) was quantified. Serial dilutions of BG01V cDNA was analyzed for amplification of 36B4 (■) and telomere repeats (●) by RQ-PCR in triplicate and the amount of cDNA plotted as a function of the average Ct. The formulas for the trend lines shown in the figure were calculated by Excel and used to estimate the expression of 36B4 and telomere repeats in hMSCs expanded in HS-2 or control media.
Figure 26:
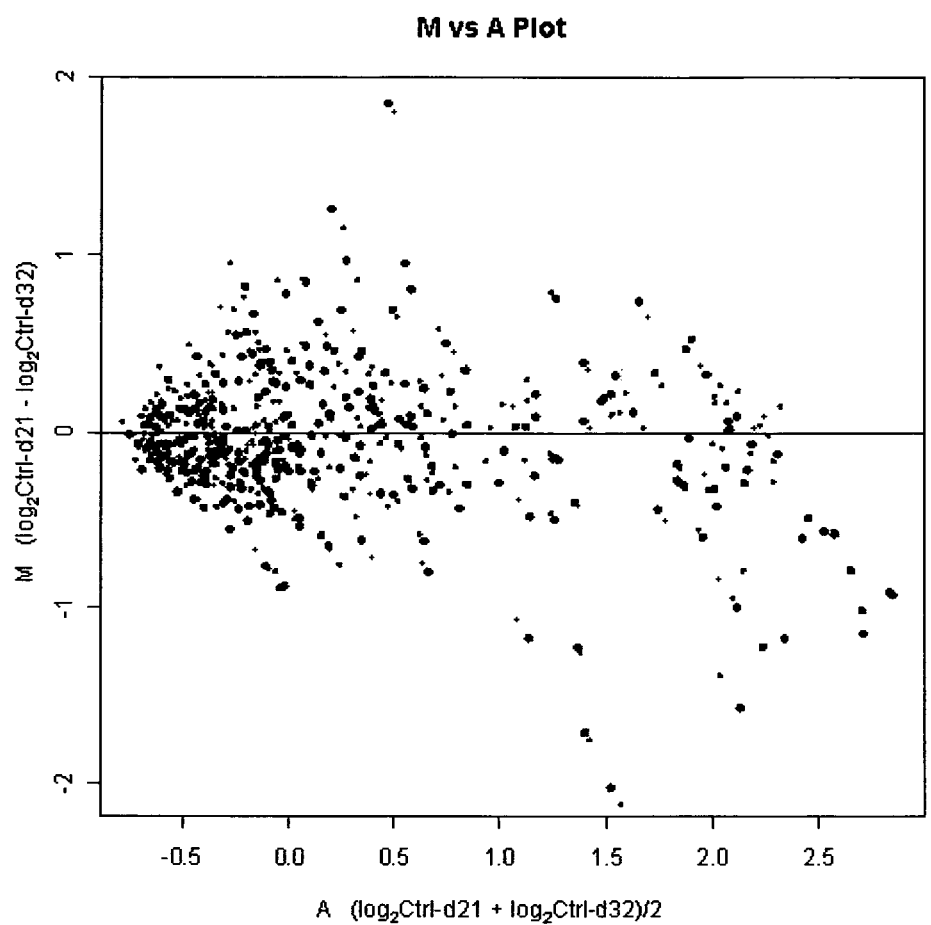
FIG. 26. MA plot after locally-weighted smoothing. Only data for Ctrl-d32 vs Ctrl-d21 is plotted. Intensities have been log-transformed and median scaled. Data before smoothing is depicted in blue and fitted values are in red.

Chromosomal DNA was isolated from cells expanded in the presence or absence of HS-2 at various time points. Cells were washed in PBS and lysed in buffer (10 mM Tris, pH 7.5, mM EDTA, 10 mM NaCl, 1% SDS 0.05 mg/ml and RNase A—DNase free) at 37° C. over night. Proteinase K (1 mg/ml) was added to the lysates, which were incubated for 5 h at 37° C. DNA was precipitated with 2 vol. of absolute ethanol and 250 mM NaCl. Precipitates were washed in 70% ethanol, dried and resuspended in $H_2O$. DNA was quantified and 12.5 ng used for amplification of both the 36B4 gene and telomeric repeats by RQ-PCR, in triplicate, as previously reported {Cawthon, 2002 #39; Guillot, 2007 #40; Cawthon, 2002 #39; Guillot, 2007 #40}. The relative expression of telomeric repeats and 36B4 was estimated from standard curves (Ct vs. log quantity) made from chromosomal DNA isolated from the human embryonic stem cell line BG01V (Invitrogen) (FIG. 22).

Stem Cell Microarray

Total RNA was purified from control and HS-2 cultures after nominated days in culture. Triplicate-labeled RNA samples were pooled (1:1:1) and used as probes on chemiluminescent cDNA arrays (GEArray S Series Human Stem Cell Gene Array, SuperArray Bioscience Corporation, Frederick, Md.). This procedure was repeated 3 times for each group for a total of 3 triplicate pooled samples per group. Arrays were analyzed using a Chemi-Smart 3000 image acquisition system (Vilber Lourmat, Cedex, France). To more fully describe the time-course effect of HS-2 on hMSC gene expression measurements, we reconstructed the genetic networks based on analyses of our microarray experiments using singular value decomposition (SVD) and principal component analysis (PCA) {Ghosh, 2002 #147}. The construction of the signature based on SVD projection is described in the Supplementary Methods (below). PCA has previously been shown to be sensitive enough to distinguish between tumour sub-types using their gene expression signature {gild, 2006 #34} and exoprotease activity {Villanueva, 2006 #41}. Fold changes in gene expression were calculated and the data hierarchically clustered by function with DAVID Bioinformatics Resources 6.7 (http://david.abcc.ncifcrf.gov/) {Huang da, 2009 #178; Dennis, 2003 #184} and a graphical heat map generated (http://api.imapbuilder.net/editor/).

Immunomodulation

Human MSCs expanded for 21 days in control or HS-2 containing media were seeded at 1×10⁵ cells/well in 96 well plates. A mixture of stimulatory and reactionary PBMCs from two different donors were added to the wells 24 h later at different hMSC:PBMC ratios and the cells incubated for 6 days before the expression of CD3+Ki67+ cells was assessed by FACS as previously reported {Rai, 2010 #155}.

Multilineage Differentiation

Human MSCs were serially passaged in HS-2 or control media for 7 passages, then lifted in trypsin/EDTA, and reseeded to compare their ability to either deposit a bone-like matrix, form lipid droplets or secrete glycosaminoglycans when stimulated with osteogenic, adipogenic or chondrogenic supplements in the absence of HS-2 as previously described {Rai, 2010 #155; Rider, 2008 #85}. In parallel cultures total RNA was isolated and the levels of mRNA transcripts for osteogenic, adipodgenic and chondrogenic biomarkers (FIG. 25) determined as previously described {Oest, 2007 #49; Rai, 2010 #155; Rai, 2007 #48; Rider, 2008 #85}. Clonal assays were also performed on hMSCs expanded in HS-2 or control media for 13 population doublings. Single cells were seeded into 96-well plates using a FACSAria (BD Bioscience) and cultured for 14 days, in the presence or absence of HS-2, and the colony-forming efficiency assessed as described above. From parallel wells, cloned hMSCs were serially passaged in the presence or absence of HS-2 and their multilineage potential reassessed as above.

In Vivo Bone Formation

Composite scaffolds containing hMSCs: HS-2- or control-expanded hMSCs (1×10⁶ cells; passage 4) were loaded onto Poly(ε-caprolactone)-tricalcium phosphate (PCL-TCP) composite scaffolds{Hutmacher, 2000 #44; Hutmacher, 2001 #45; Rai, 2004 #46; Rai, 2005 #47; Rai, 2010 #155} (Osteopore International) and placed into 24-well culture plates, mixed with Fibrin Tisseel Sealant (Tisseel kit, Immuno, Austria) in a 3:1 ratio as previously described {Rai, 2004 #46}. After cell seeding, 1 ml of fresh culture medium was added to each well and cells were incubated in humidified atmosphere at 37° C. and 5% $CO_2$ overnight prior to transplantation.

Rat Femoral Defect Model:

To determine the efficacy of HS-2 expanded hMSCs for bone healing, composite scaffolds containing hMSCs were transplanted into bilateral segmental critical-sized femoral defects in nude rats. The research protocol for the use of 18 male, CBH/Rnu rats, weighing 220-260 g was approved by the Institutional Animal Care and Use Committee, Agency for Science Technology and Research, Singapore following all appropriate guidelines. All surgical procedures were performed as previously established {Oest, 2007 #49; Rai, 2010 #155; Rai, 2007 #48}. Briefly, after exposing the femur via a longitudinal incision over the proximal hindlimb, femurs were stabilized with custom modular fixation plates and 8 mm bilateral segmental critical-sized defects were created with a miniature oscillating saw. Each rat received an hMSC-seeded PCL-TCP scaffold in one of the femoral defects, with the contralateral femoral defect receiving an HS-2-expanded, hMSC-seeded, PCL-TCP scaffold. After euthanasia at 3 and 7 weeks, samples were harvested and stored in 10% neutral buffered formalin for subsequent 2D radiography (n=6 per group), 3D micro-computed tomography (μ-CT) (n=6 per group), cell survival analyses (n=3/group), histology (n=3 per group) and immunohistochemistry (n=3 per group).

Paraffin Histology, Cell Survival, 2D Radiography and μ-CT Analysis

Paraffin histology, cell survival analysis and imaging of femurs were performed immediately after surgery and again at weeks 3 and 7 as previously published {Rai, 2010 #155}.

Resin Histology

Selected femurs were subjected to undecalcified resin processing/embedding in methylmethacrylate as per our previously established methods {Sawyer, 2009 #80}. Transverse sections were cut to 5 μm and stained with MacNeal/von Kossa, and examined under an Olympus Stereo (SZX12) microscope.

Immunohistochemistry

The procedures were performed according to our previously established methods {Sawyer, 2009 #80}. Tissue sections were incubated with the primary antibodies for osteocalcin (Abcam, Cambridge, UK), or the same concentration of mouse IgG (Caltage Laboratories, Burlingame Calif., USA; as negative control).

Statistical Analysis

Data are presented as means±S.D for at least three independent experiments, each measured in triplicate. Two-tailed unpaired t-tests were performed and significant differences between the control and HS-2 groups are marked with a single (p<0.05), double (p<0.005) or triple asterisk (p<0.0001).

Results

HS-2 Increases hMSC Growth and Maintains their Viability

We have previously described an FGF-2-binding HS(HS-2) {Brickman, 1995 #28; Nurcombe, 1993 #29} with potent bioactivity towards neural precursor cells. Because FGF-2 is a potent mitogen for stem cells, including hMSCs, we examined the biological activity of HS-2 in stimulating the expansion of hMSCs. In this study we investigated whether HS-2 can support and accelerate the ex vivo expansion of hMSCs to yield therapeutic numbers of cells without loss of multipotentiality. Furthermore, we determined whether HS-2 expanded cells were able to enhance bone formation when transplanted in vivo.

Pilot experiments revealed that the optimal dosage for HS-2 in enhancing cell proliferation is in the ng/ml range with 160 ng/ml yielding maximal stimulatory activity (FIG. 23), consistent with our previous studies {Dombrowski, 2009 #82}. HS-2 at 160 ng/ml increased the proliferation of sub-confluent hMSCs over a 6-day period by ~65% (p<0.005) (FIG. 15A), consistent with microscopic observations (FIG. 15B). This increased cell number is due in part to a modest increase in cell viability (data not shown) and reduced apoptosis based on Annexin V staining (FIG. 15C). To discriminate between HS-2 effects on cell cycle kinetics versus the proliferation-quiescence transition, we performed serum deprivation experiments (FIGS. 15D & E). Serum-deprived quiescent cells were stimulated with serum in the absence/presence of HS-2. Serum stimulation results in S-phase entry by 15 h in the absence/presence of HS, however the number of cells in S-phase is much greater upon HS-2 stimulation (FIG. 15D). Similarly, HS-2 increased the amount of G2/M cells but not their temporal appearance after serum stimulation (FIG. 15E). Thus HS-2 does not affect the temporal progression through G1 resulting in S-phase and G2 entry but rather the number of cells that enter the cell cycle from G0 following serum stimulation.

Because HS-2 appears to affect the G0/G1 transition, we addressed whether HS-2 could improve the proliferative efficacy of FCS as measured by WST-1 assays that monitor proliferation-related metabolic activity (FIG. 15F). Gradually decreasing FCS concentrations from 10 to 1% resulted in reduced proliferative activity. However in the presence of HS-2, the mitogenic activity of FCS was markedly improved; for example, activity levels at 2.5% FCS with HS-2 mirror those with 7.5% FCS without HS-2. Furthermore, activity levels at 5% FCS or higher all exhibited more robust proliferative activity with HS-2 compared to the normal dose of 10% FCS. Interestingly, supplementation with HS-2 caused hMSCs to release significant amounts of FGF2 into the culture medium, suggesting the sugar-triggered formation/enhancement of an autocrine loop (data not shown). Collectively, these results indicate that HS-2 increases cell number by stimulating a population of normally quiescent cells to enter the cell cycle and sustain their proliferation.

To determine whether HS-2 supplementation affects the immunophenotypic profile of hMSCs, we performed flow cytometric analysis of sub-cultured cells. We first established profiles on early passage hMSCs and noted high expression of CD73 and CD105 and moderate expression of CD49a and STRO-1 (FIG. 16A). These cells where then further expanded in control or HS-2 supplemented media and again analyzed for STRO-1 expression (FIGS. 16B & C). HS-2 treatment resulted in significantly greater STRO-1 expression, and especially the STRO-1+bright population. Moreover, in a separate experiment, we cultured low passage hMSCs continuously in HS-2 media for up to 10 population doublings (FIG. 16D) and noted a marked increase in the proportion of STRO-1-expressing cells. This was in contrast to cells maintained in control media, whose proportion of cells expressing STRO-1 continued to decline. This finding was corroborated by colony efficiency assays, with HS-2-expanded cells after 10 population doublings forming ~50% more colonies compared to cells cultured in control media (FIG. 16E). Collectively these data suggest that HS-2 has a pronounced effect on the STRO-1 positive population that is maintained over time in culture.

Figure 17:
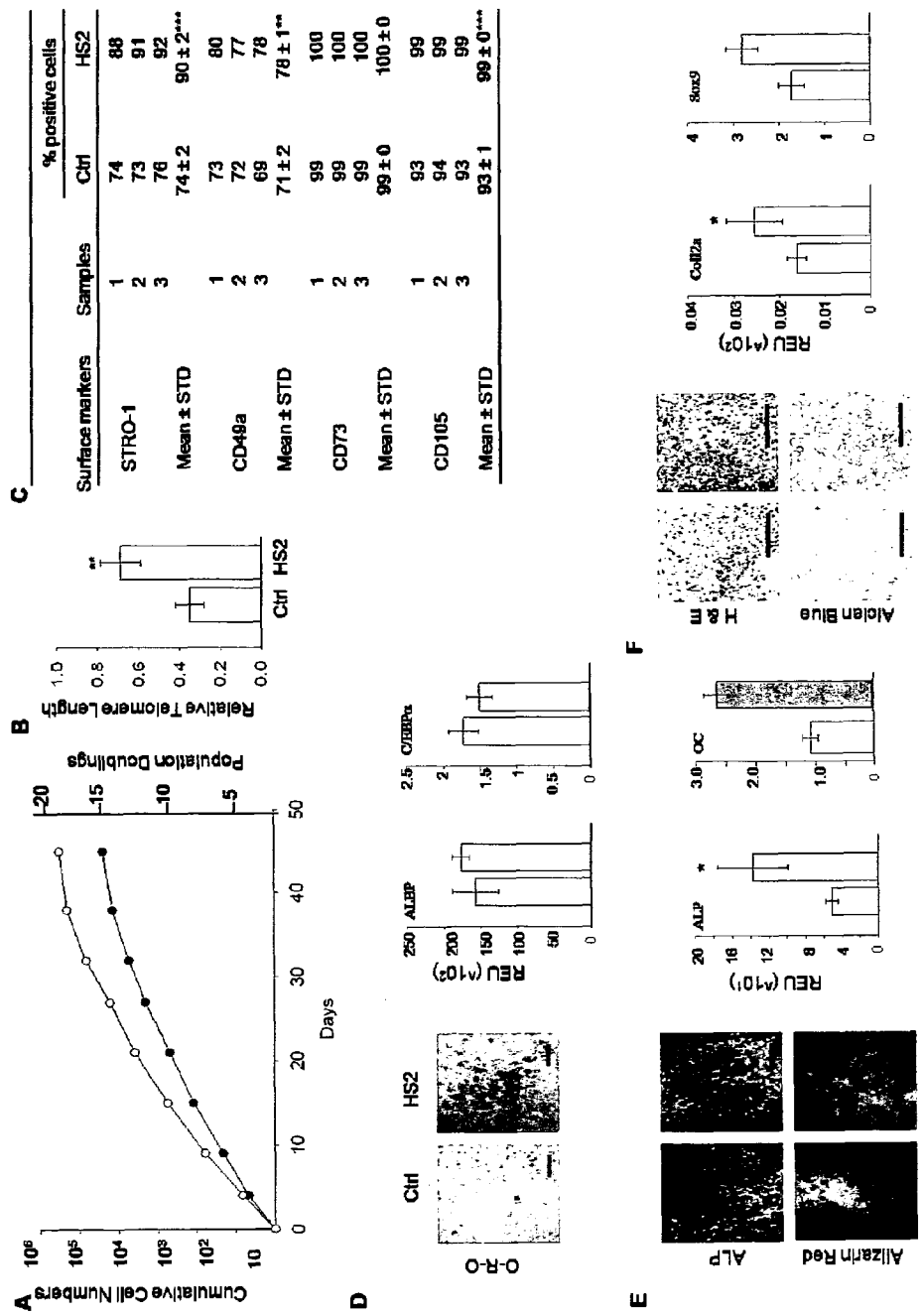
FIG. 17. Presence of HS-2 enriches for a subpopulation of more naïve stem cells with longer telomeres during large-scale expansion of hMSCs. (A) Human MSCs were expanded in control or HS-2 media for 45 days and both the cumulative number of cells produced by a single cell and population doublings plotted against time. (B) Average telomere length of hMSCs expanded in control or HS-2 for 15 population doublings. The values are normalized to the length of telomeres in the original primary hMSC cultures. (C) Expression of surface markers in cultures of cells from 3 different human donors expanded for 40 days in control or HS-2-containing media. Asterisks denote significance at the 0.0001 (*) or 0.005 () level. (D-F) Differentiative potential of hMSCs expanded in control (white bars) or HS-2 (grey bars) media for 38 days as in A. Expanded cells were then differentiated for 28 days in either adipogenic (D), osteogenic (E) or chondrogenic media (F). Adipogenesis was measured by Oil-Red-O staining (Scale bar=1 mm) and with quantitative PCR for both the CCAAT/enhancer binding protein-a (C/EBPa) and adipocyte lipid binding protein (ALBP); osteogenesis was measured by alkaline phosphatase, alizarin red (Scale bar=1 mm) and as well as quantitative PCR for both alkaline phosphatase (ALP) and bone sialoprotein 2 (BSPII); chondrogenesis was measured by H&E and alcian blue staining (Scale bar=500 μm) as well as quantitative PCR for both collagen2a1 (Coll2a) and SOX9.

Human MSCs Expanded Long-Term in HS-2 Proliferate More Readily Yet Retain Their Multipotency As HS-2 has a potent early effect on the growth of hMSCs cultures, we next sought to determine its long-term effects. Expansion of hMSCs for clinical use typically requires cells to be cultured for up to one month to achieve a therapeutic dose (http://osiris.com). We expanded hMSCs in either HS-2 or control media following established protocols {Haynesworth, 1992 #32; Jaiswal, 1997 #33; Haynesworth, 1992 #32; Jaiswal, 1997 #33}. Cultures supplemented with HS-2 resulted in an order of magnitude more cells than controls after only 21 days (FIG. 17A). To determine the long-term effect of HS-2 supplementation on hMSCs, we performed a series of assays that examined telomere length, CFU-F frequency, immunophenotype, and multilineage differentiation potential. Cells expanded for 15 PDs in HS-2 had significantly longer telomeres than cell expanded in control media (FIG. 17B). Notably, no telomerase activity could be detected in these cells irrespective of the culture treatments, as previously reported (data not shown) {Shi, 2002 #11; Simonsen, 2002 #12}. Also, repeated passaging was not associated with karyotypic abnormalities (data not shown).

To test whether prolonged exposure to HS-2 adversely affected the hMSC phenotype, surface marker expression was analyzed after at least 15 PDs. The expression of STRO-1, CD49a and CD105 was increased significantly in the presence of HS-2, and CD73 remained unchanged (FIGS. 17C & D), despite the fact that HS-2 supplementation had yielded 13-fold more cells by this time (FIG. 17A). We next sought to determine the adipogenic (FIG. 17E), osteogenic (FIG. 17F) and chondrogenic (FIG. 17G) potential of these cells when cultured in the appropriate differentiating media using a combination of histological and PCR-based approaches. Notably, HS-2-expanded cells had similar, or in some cases, increased multipotentiality compared to control. Moreover, the ability of these cells to enter either the osteogenic or chondrogenic lineage was particularly pronounced. These data show that HS-2 significantly increases the proliferation of a subpopulation of highly multipotent (STRO-1 expressing) hMSCs that have longer telomeres.

HS-2-Expanded hMSCs Retain CFU-Fs and are Multipotential after Single Cell Cloning To rigorously demonstrate that HS-2 supplementation is capable of targeting the expansion of true mesenchymal stem cells, rather than a mixed populations of progenitors, we evaluated colony formation and multipotentiality of single cell clones isolated from hMSCs previously expanded for 13 PDs in either HS-2 or control media. Single cells were seeded into 96 multi-well plates and cultured for 2 weeks. The cells expanded in HS-2 showed higher rates of colony formation (12%) than cells in control media (7%; FIG. 18A). The multilineage potential of parallel colonies was also assessed by adipogenic (lipid accumulation), osteogenic (alizarin red staining) and chondrogenic (alcian blue staining) assay (FIG. 18B). These data further confirm that hMSCs expanded in the presence of HS-2 retain their multipotentiality over control cells expanded for the same number of PDs.

Expansion of hMSCs in HS-2 Maintains Their Naïvety

Figure 19:
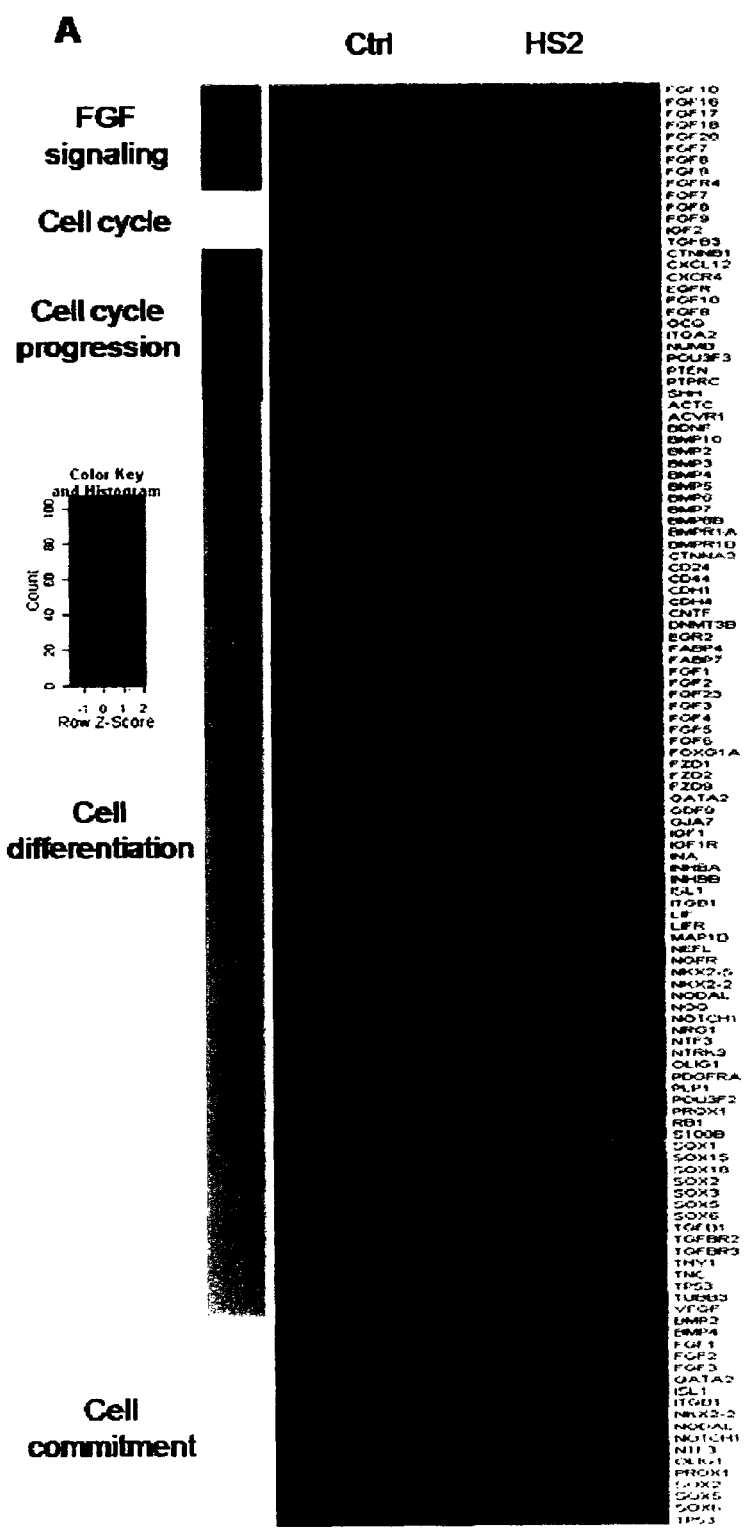
FIG. 19. HS-2 protects hMSC cultures against the temporal lose of stem cell gene expression. (A) Hierarchical clustering analysis of gene expression of hMSCs maintained in either control media or HS-2 measured by chemiluminescent GEArray (Stem Cell SuperArray #HS601.2). (B) Singular value decomposition analysis of stem cell-related gene expression. Data were log-transformed and corrected for cross-chip variations. MSCs grown in HS-2 (open circles) for longer periods cluster with MSCs grown in control media (closed circles) for shorter times. (C) Significantly regulated genes are tabulated.

Qualitative measures of sternness in hMSC are most often reported based on assessment of adherence to tissue culture plastic, immunophenotypic profile and multilineage assays {Dominici, 2006 #185} and in vivo bone formation {Shi, 2002 #11}. We also utilized gene profiling (FIG. 19A) and principal component analysis {Villanueva, 2006 #41} (PCA; FIG. 19B) using a stem-cell specific array to assess the effects of HS-2. A heat map based on hierarchical clustering by function revealed that genes associated with cell cycle progression and mitogenic signalling were down-regulated in controls, whereas genes involved in cell commitment and differentiation were down-regulated in HS-2. Of particular note, amongst the genes most up-regulated, those involved in cell adhesion and growth are prominent whereas amongst the genes most down-regulated, members of the Wnt and TGF families are prominent.

Array data was then projected onto the first two maximally-variant singular vectors to create an expression signature by singular value decomposition (SVD) (FIG. 19B) {Alter, 2000 #36; Holter, 2000 #37} (Supplementary Methods). These data show that hMSCs expanded in the presence of HS-2 (open circles) for 21 days had a distinctive gene expression signature and did not cluster with cells from other treatments, like control cells cultured for 45 days. However, clustering between cells cultured for 32 or 45 days in the presence of HS-2 and control cells at 21 or 32 days was apparent. This suggests that HS-2 yields a stem cell gene signature typical of younger control cells. To determine whether the HS-2 effect was robust, the stem cell gene expression signature at day 21 from two other donors was compared to the first donor. They also clustered together on the basis of treatment. This indicates that the effects of HS-2 were not donor-specific, and that gene expression signatures produced by SVD can be used to reliably compare cells from different donors.

HS-2-Expanded hMSCs Stimulate Robust Bone Formation in Orthotopic Defects

Figure 20:
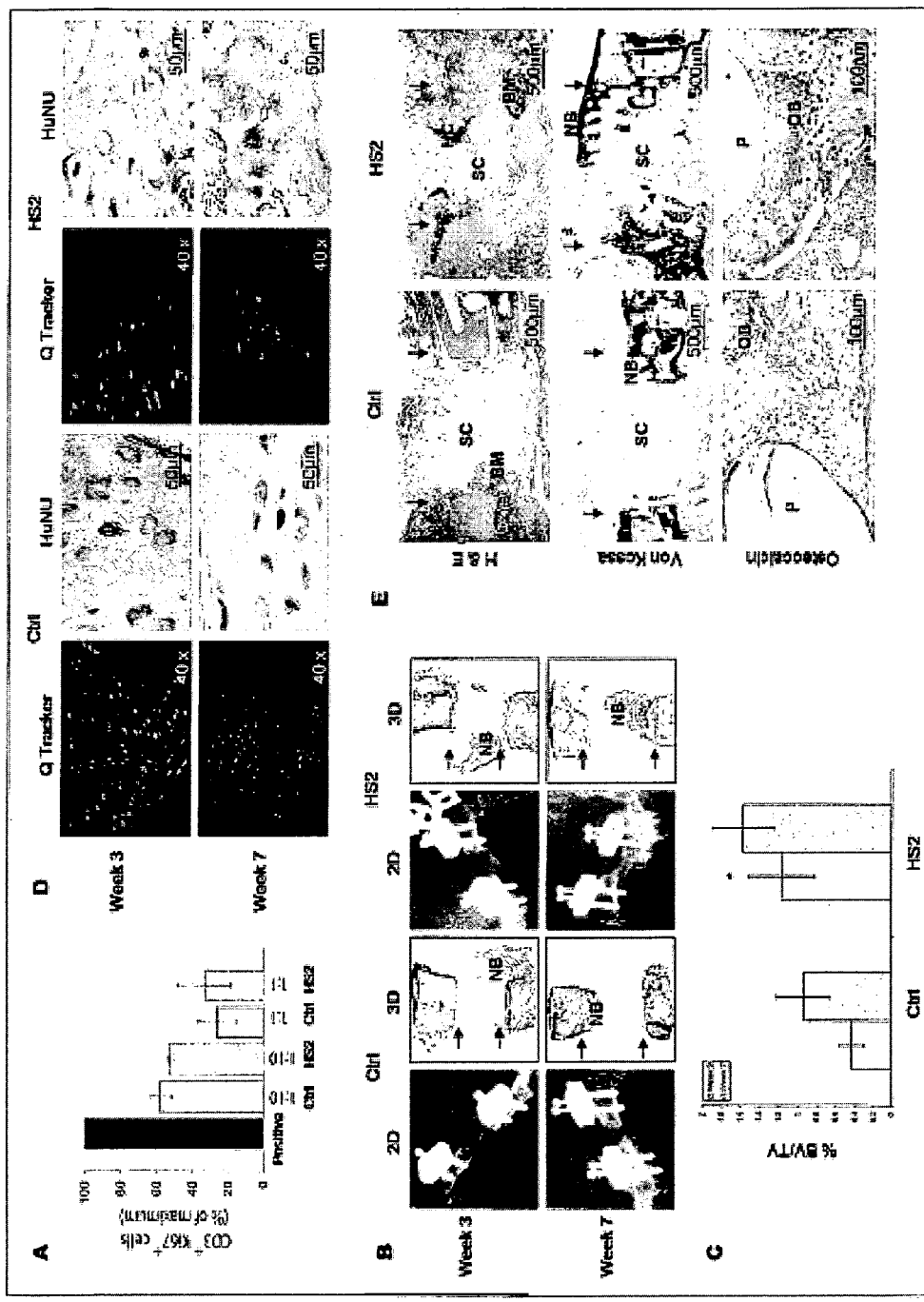
FIG. 20. hMSCs cultured in HS-2 retain their immunomodulatory capabilities and increase bone formation in vivo. (A) Immunomodulatory activity of hMSC cultured in control or HS-2 supplemented media for 21 days. A mixture of stimulatory and reactionary PBMCs from two different donors were added to the wells at different hMSC:PBMC ratios after a further 24 h, and then 6 days later the expression of CD3+Ki67+ cells assessed by FACS. The positive control represents the maximum number of CD3+Ki67+ cells obtained in the absence of hMSCs. Readings in duplicate for each experiment and the graph is mean with ±SD of two separate experiments. (B) Representative μ-CT images of femurs treated with HS-2 expanded hMSCs (HS-2) and control media (Ctrl) at 3 and 7 weeks. (C) Percent bone volume at weeks 3 and 7 as determined by CTan software. Results are expressed as mean±SD, n=6 for each treatment group per time point. (D) Representative DAPI-stained cryosections of femurs treated as in B, to reveal surviving hMSCs in the defect. DAPI stains the nuclei of cells blue, while the hMSCs that were pre-labelled with QTracker®, fluoresce red. (E) Representative histological sections of femurs treated as in B at week 7. NB: New bone, BM: Bone marrow, SC: Scaffold, HC: Hypertrophic chondrocytes, P: Pores of scaffold and OB: Osteocalcin-positive osteoblasts. Arrows delineate the ends of the defect.

As hMSCs have been shown to exert immunosuppressive effects {Aggarwal, 2005 #214; Shi, 2010 #187}, we first sought to determine whether continuous expansion in HS-2 had any adverse effect (FIG. 20A). Human MSCs were expanded for 21 days in either HS-2 or control and then challenged with a mixture of stimulatory and reactionary PBMCs from two different donors at different hMSC:PBMC ratios for 6 days after which CD3+Ki67+ expression was assessed. HS-2 did not impair the immunosuppressive effects of the hMSCS.

We next sought to determine whether long-term ex vivo expansion of hMSCs in HS-2 affected their therapeutic utility when transplanted into a clinically relevant in vivo bone defect model. Bone formation within the osseous defect was assessed by X-ray and µ-CT imaging at 3 and 7 weeks post-surgery and demonstrated that hMSC transplantation resulted in bone repair that was more prominent with HS-2-expanded hMSCs (FIG. 20B).

Quantitative analysis of the µ-CT images showed that new bone formation was accelerated in defects treated with HS-2-expanded hMSCs (FIG. 20C). Bone bridging was not observed in any of the treated femurs, as this occurs only at later stages of bone regeneration.

To assess the in vivo survival of the implanted hMSCs, selected defects were treated with cells that were pre-labeled with Qtracker® fluorescent nano-particles. At 3 weeks post-transplantation, labelled hMSCs were present within the bone defect site of all treated femurs (FIG. 20D). Notably, the cytoplasmic label was only found co-localized to DAPI-positive cells, confirming that it was retained by the transplanted hMSCs. Immunostaining with a human nuclei-specific antibody further verified the presence of surviving hMSCs within the defect site. By 7 weeks, the only labeled cells still present in the defect site were from hMSCs expanded in HS-2.

The healing potential of the transplanted hMSCs was further verified 7 weeks post-surgery by histological assessment. H&E sections of defects receiving HS-2-expanded hMSCs revealed new bone-like tissue, bone marrow and hypertrophic chondrocytes (indicating endochondral ossification) infiltrating the defect site from both the host bone interface and the subcutaneous interface (FIG. 20E). Von Kossa-stained sections confirmed the presence of mineralised bone-like tissue (stained black) in the HS-2 cell group that bridged the majority of the defect and infiltrated the scaffold pores. Similarly, abundant osteocalcin-rich tissue was also evident throughout the defect site. In contrast, defects treated with control-expanded hMSCs resulted in little mineralized tissue that was largely devoid of von Kossa and osteocalcin staining (FIG. 20E). Thus HS-2-expanded hMSCs retain their ability to stimulate robust bone formation despite their extensive ex vivo expansion. Moreover, the enhanced survival of the HS-2-expanded hMSCs at the defect may have resulted in a larger or more persistent secretion of bioactive molecules, resulting in improved bone formation {Meirelles Lda, 2009 #58}.

HS-2 Robustly Expands hMSCS Isolated from Unfractionated Bone Marrow Aspirates

Figure 15:
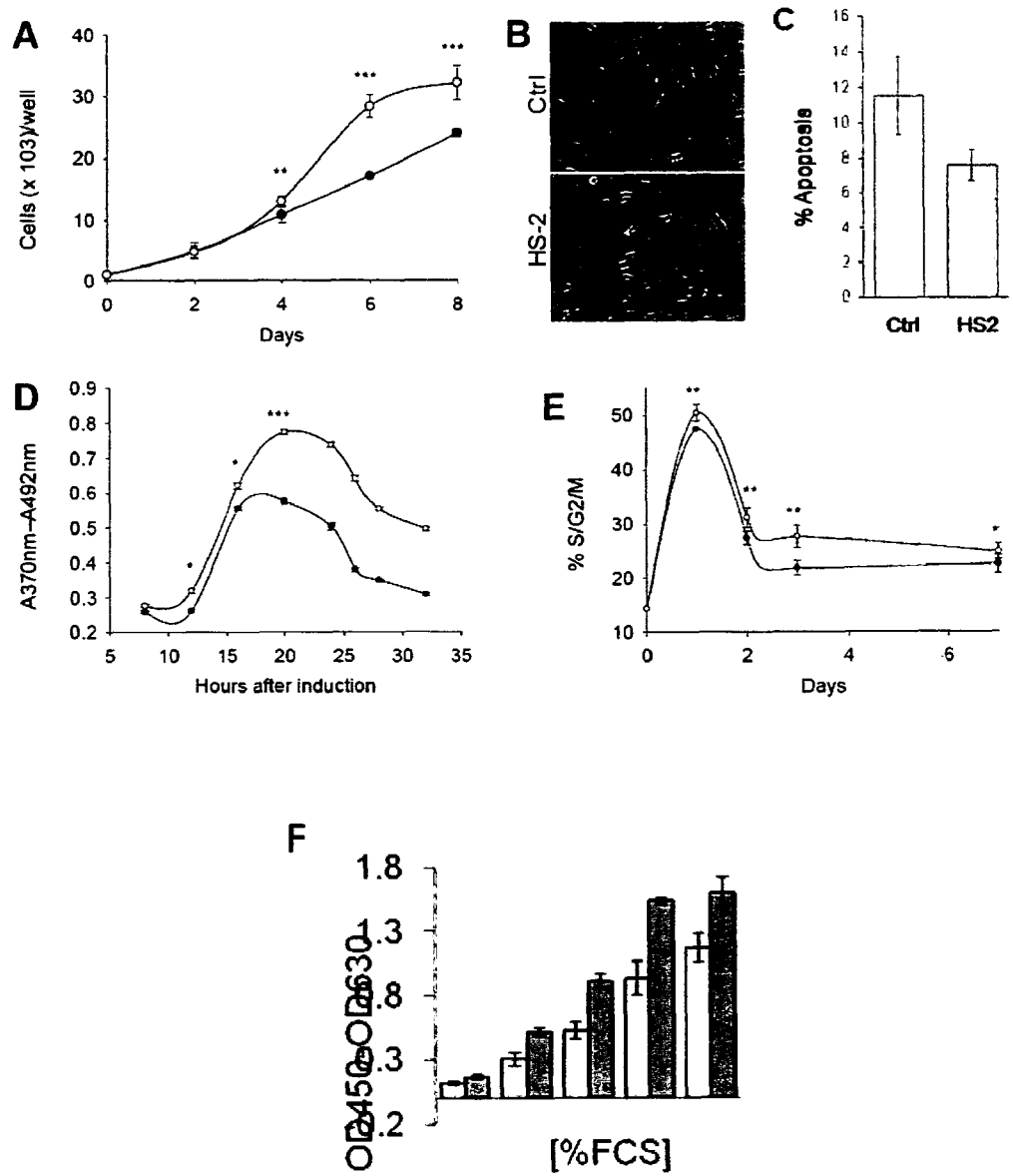
FIG. 15. Short-term exposure to HS-2 increases the proliferation of hMSCs. (A) Proliferation of cells exposed to increasing doses of HS-2; 160 ng/ml was used subsequently. Assays were in triplicate. (B) Phase contrast micrograph of cells cultured in control (upper) and HS-2 containing media (lower), bar=200 μm. (C) Viability levels as measured by annexin and AAD-7 staining using GUAVA software after 8 days exposure to HS-2. (D) Incorporation of BrdU during short-term exposure to control or HS-2 after serum deprivation. (E) Proportion of cells in S/G2/M phases of the cell cycle when cultured in HS-2 over 3 days. Control (black circles) and HS-2 (open circles). Error bars represent the standard deviation, n=3. (F) WST-1 metabolic assay of hMSCs exposed to increasing concentrations of FCS, with (grey bars) or without exogenous HS-2 (open bars). Experiments in triplicate.
Figure 16:
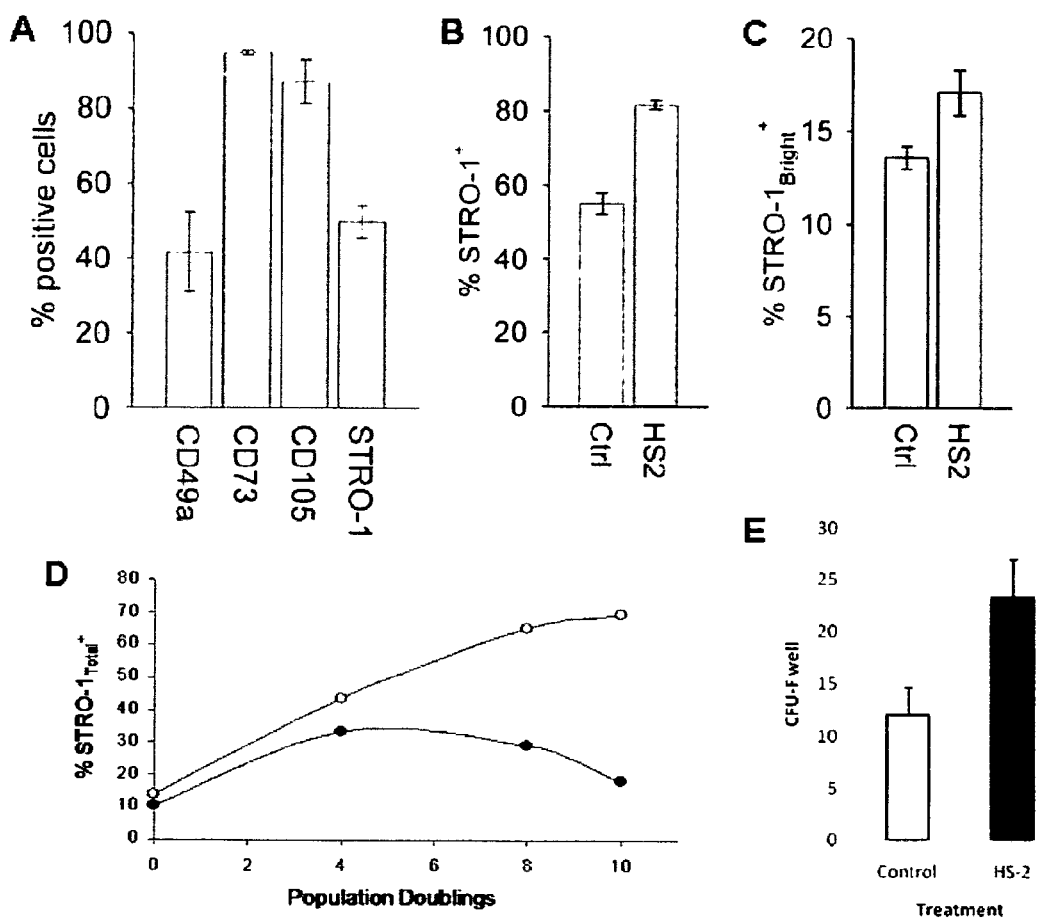
FIG. 16. Exposure to HS-2 increases the recovery of CFU-F hMSCs from bone marrow aspirates and stimulates expansion of the STRO-1 positive subpopulation. (A) Immunophenotype of early hMSCs as established by FACS. (B) Early hMSCs were expanded and quantitated for the proportion of sorted cells that were STRO-1$^+$ or (C) STRO-1$^{+bright}$. Control in white bars and HS-2 in grey bars. Error bars for B and C represent SD, n=3. (D) Low passage MSCs were placed into either control medium (black circles) or HS-2 (open circles) and the proportion of cells positive for STRO-1 monitored by FACS for 10 population doublings. (E) Cells after 10 doublings we subjected cells to colony efficiency assays. The black bar represents cells expanded in HS-2, the open bar cells in control media. Error bars represent SD, n=3.
Figure 21:
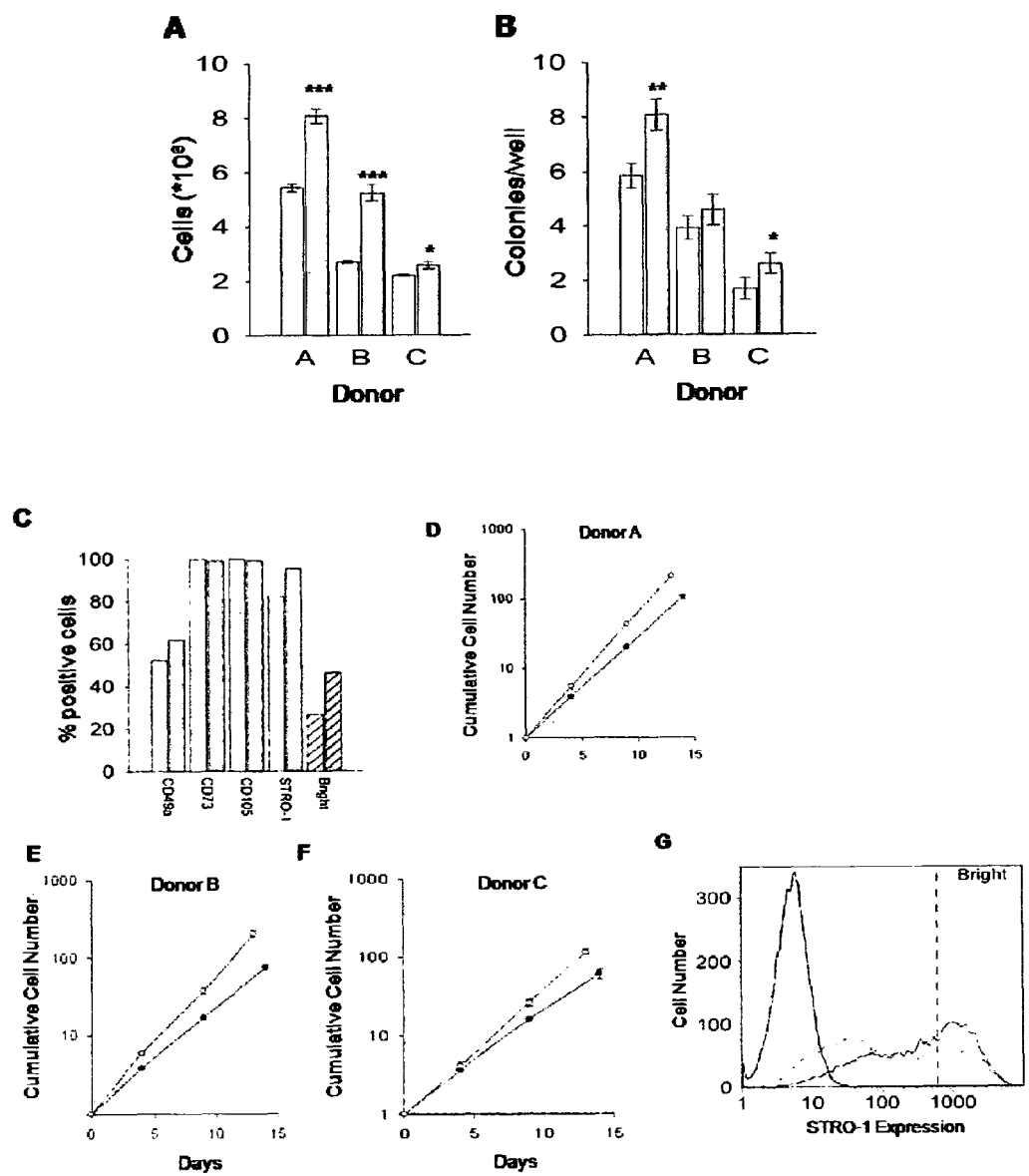
FIG. 21. Exposure to HS-2 increases the recovery of CFU-F hMSCs from bone marrow aspirates and stimulates expansion of the STRO-1 positive subpopulation. (A) Recovery of primary CFU-F hMSCs from 3 different bone marrow mononuclear cell donor batches in control or HS-2-containing media and (B) the number of colonies from 1:15 diluted cultures in control and HS-2-containing media. Significant differences between the control and HS-2 groups are marked with a single (p<0.05, t-test) or triple asterisk (p<0.0001, t-test). (C) Representative example of surface marker expression in CFU-F hMSCs recovered in control or HS-2-containing media. (D-F) Increases in the cumulative number of cells for three different pools of hMSCs. Low passage hMSCs were plated at 5000 cells/cm$^2$ and cultured in media with or without 160 ng/ml HS-2 to sub-confluence, whereupon cells were trypsinized, counted and reseeded at 5000 cells/cm$^2$ in the respective media. This was repeated for a period of two weeks. Numbers are cumulative increases in cell number starting from one cell. (G) FACS analysis of the STRO-1 expression profile of CFU-F hMSCs recovered in control (green) or HS-2-(blue) containing media after 6 further days. Isotype control is indicated by red line. Control in white bars and HS-2 in grey bars. Error bars for H and I represent SD, n=3. (J) Low passage MSCs were placed into either control medium (black circles) or HS-2 (open circles) and the proportion of cells positive for STRO-1 monitored by FACS for 10 population doublings.

As HS-2 proved effective in the culture expansion of muttipotent hMSCs, we next sought to determine whether cells isolated directly from unfractionated bone marrow also responded positively to HS-2 supplementation with a view to determining its direct clinical utility. Aspirates sourced from three separate healthy donors contained plastic-adherent hMSCs that strongly responded to HS-2 both in terms of their proliferative capacity and their colony forming ability (FIG. 20 A&B) thus corroborating results obtained with established hMSC cultures (FIGS. 15 & 16). Flow cytometric assessment revealed that none of the cells expressed the hematopoietic markers CD34 or CD45 (data not shown), but did express the hMSC markers CD49a, CD73, CD105 and STRO-1 (FIGS. 21 C&D). As the majority of the CFU-Fs derived from bone marrow mononuclear cells (BMMNCs) are contained within a subpopulation of cells with high STRO-1 expression (STRO-1+bright) {Gronthos, 1995 #31; Gronthos, 2003 #9} we determined the effect of HS-2 on the proportion of STRO-1+bright cells (FIGS. 21 C&D). The mean STRO-1+bright content in HS-2 expanded cells was 46.4%, compared to 26.6% for cells expanded in control media (FIG. 21D). Thus HS-2 preferentially promotes the expansion of a subpopulation of STRO-1+bright hMSCs contained within bone marrow aspirates.

To further assess the ability of HS-2 to expand hMSCs, low passage cells isolated by plastic adherence from the three bone marrow donors were cultured for two weeks in the presence or absence of HS-2. In all three cases, supplementation with HS-2 accelerated the cumulative increase in cell numbers in line with the previous results on establish hMSCs cultures (FIGS. 15 & 16).

Discussion

The results of this study show that an embryonic heparan sulfate, HS-2, can be used to preference the rapid expansion of true hMSCs without the need for prospective immunosorting, or the use of a variable cocktail of protein factors that invariably results in heterogeneous cultures. Furthermore, these HS-2-expanded hMSCs display superior therapeutic utility when transplanted into a clinically relevant model of orthopaedic trauma. Thus the use of HS-2 is particularly attractive as a stand-alone method to selectively enrich and then propagate the most therapeutically desirable hMSC sub-population.

Current strategies employed to generate hMSCs for clinical use rely on their isolation by adherence to plastic, followed by lengthy ex vivo expansion prior to their re-implantation. This process is required due to the extremely low frequency of hMSCs in adult bone marrow {Caplan, 2009 #59; Gronthos, 2003 #9; Pittenger, 2004 #6; Psaltis, 2010 #102}. This is further exacerbated by both the age-related loss in hMSC growth potential {Ciapetti, 2006 #735} and the fact that many hMSCs remain quiescent when isolated and cultured {Terai, 2005 #38}. As such, strategies are required that allow for the ex vivo expansion of this particular sub-population in order to achieve an efficacious treatment modality. To address this need, a range of isolation and expansion methodologies have been trialled including prospective immunoselection using a range of mAb to antigens that include STRO-1 {Dennis, 2002 #736; Gronthos, 1994 #740}, STRO-3 {Gronthos, 2007 #755} CD49a {Rider, 2007 #508; Deschaseaux, 2003 #809}, CD146 {Filshie, 1998 #751; Shi, 2003 #747}, SSEA4 {Gang, 2009 #357}, LNGFR/CD271 {Jones, 2008 #839} and VCAM-1 {Gronthos, 2003 #9}, culture expansion with factors such as FGF-2 {Solchaga, 2010 #769; Solchaga, 2005 #15; Walsh, 2000 #18; Lee, 2009 #376} and more recently the use of platelet-derived products {Avanzini, 2009 #326; Capelli, 2007 #510; Doucet, 2005 #55; Kocaoemer; 2007 #549; Schallmoser, 2007 #516; Vogel, 2006 #561} and defined specialty medias {Hudson, 2010 #270}. Despite extensive research into these strategies, their widespread acceptance is yet to take place.

Of the targets for immunoselection, the STRO-1+bright subpopulation has been shown to enrich for clonogenic stromal cells (CFU-Fs) {Gronthos, 1994 #740} but this requires lengthy cell sorting procedures. In contrast, HS-2 treatment that avoids mAb-based preselection, increased the proliferation of STRO-1+hMSCs, including the STRO-1+bright subpopulation, after only one passage. Notably, continuous passaging in HS-2 resulted in a further increase in STRO-1 expression (from ~45% to ~70%) that was not replicated with standard culture conditions. Thus, in a therapeutic setting where large-scale expansion of hMSCs is required to obtain an efficacious dose, the presence of HS-2 will greatly reduce the culture time needed. Moreover, HS-2 preferences the expansion of highly multipotent hMCS that are known to be the source of paracrine factors which contribute to their therapeutic value {Caplan, 2009 #59}. Indeed, critical-sized bone defects treated with HS-2-expanded hMSCs showed greatly improved bone repair, with the transplanted cells surviving within the defect site for up to 7 weeks. Notably, appreciable new bone formation was observed as early as 3 weeks post transplantation but without the treatment variability we have previously reported {Rai, 2010 #155}. The use of HS-2 to expand the hMSCs also precluded the need to predifferentiate the cells, a strategy that appears to improve healing outcomes in some models. Of particular note is that despite achieving large-scale expansion of multipotent hMSCs using HS-2 supplementation, these cells retain their immunosuppressive capabilities {Meirelles Lda, 2009 #58}; an ability that is associated with higher chances of survival in vivo {Stenderup, 2001 #8}.

Exogenous FGF-2 has been shown to regulate hMSC self-renewal {Ahn, 2009 #850; Sotiropoulou, 2006 #622; Tsutsumi, 2001 #17}, but its long-term use also increases their heterogeneity {Walsh, 2000 #847} and upregulates HLA-class I and induces low HLA-DR expression {Sotiropoulou, 2006 #622}, so impairing its clinical use. In contrast, we show that continuous supplementation with HS-2 similarly regulates hMSC self-renewal yet greatly improves the level of homogeneity, making it particularly suited to use in regenerative medicine.

These highly charged HS molecules can be extracted and purified through a series of well-established enzymatic, chemical and chromatographic steps that preclude infectious agents such as bacteria, viruses and prions. In contrast to protein growth factors, HS is resilient to a range of bioprocessing procedures, being thermally stable and chemically resistant {Luong-Van, 2007 #854; Luong-Van, 2006 #855}, making it well suited not only as a culture supplement but for a range of biomedical applications. The use of HS-2 to greatly expand hMSC preparations with reduced heterogeneity and superior regenerative potential should advantage their future clinical application.

Supplementary Methods

Cell assays using a GUAVA PCA-96 benchtop flow cytometer. At every passage, and during proliferation assays, cell numbers were determined using the Viacount FLEX reagent and software. For analysis of surface markers, cells were trypsinized, blocked for 1 h (PBS, 5% FCS, 1% BSA and 10% human serum), resuspended in staining buffer (PBS, 2% FCS, 0.02% $NaN_3$) and incubated with mouse anti-STRO-1 (R&D Systems) or mouse IgM control (Caltag) followed by PE-conjugated goat anti mouse-IgM (Caltag) or with PE-conjugated mouse anti human CD49a, CD73, CD105 (all BD bioscience) and an IgG control (Caltag). Cells were then analyzed from 2000 events using the Guava software. For cell cycle analysis, the cells were serum-starved and the media changed as previously described, then trypsinized after the time points mentioned, washed twice in PBS/1 mM EDTA, fixed in ice cold methanol and stored at 4° C. until staining. Fixed cells were washed once in staining buffer (see above), stained in a BD RNaseA/PI staining solution (BD Bioscience) and analyzed using the Guava software. For apoptosis assays, cells were cultured for 8 days before the expression of annexin and AAD-7 were measured using the Guava software.

Differentiation assays. For adipogenic differentiation, cells were seeded (18,000 cells/$cm^2$) in 12-well plates and cultured to confluence at which time media was changed to adipocyte maintenance media (4,500 mg/l glucose) with or without (control) 1 μM dexamethazone, 10 μM insulin, 20 μM indomethazine and 115 μg/ml 3-isobutyl-1-methylxanthine and cultured for 28 days and stained with oil-red-O. For osteogenic differentiation, cells were seeded (3,000 cells/$cm^2$) in 12-well plates for 24 h, then changed into maintenance media with or without (control) 10 nM dexamethazone, 10 mM β-glycerol-phosphate and 25 μg/ml L-ascorbate-2-phosphate, cultured for 28 days and stained with alizarin red or alkaline phosphatase. For chondrogenic differentiation, cells (250,000 cells/tube) were pelleted in chondrogenic media (Cambrex) with or without (control) 10 ng/ml TGF-β3 in 15 ml tubes and cultured for 28 days where cells were fixed, embedded, mounted and stained with H&E and alcian blue. Details on staining and histology are described in the Supplementary Methods which correspond to the methods of Li et al[1]. For all differentiation experiments, total RNA was isolated at day 28 and lineage specific gene expression analyzed by quantitative PCR.

Staining and Histology. Oil-Red-O staining of triglyceride; cells were washed in PBS and fixed in 4% paraformaldehyde (PFA) (Sigma) in PBS for 1 h, washed in water, stained with 3.6 μg/ml Oil-Red-O (Sigma) in 60% isopropanol for 1 h and washed in water. Alizarin Red staining; cells were washed in PBS, fixed in 4% PFA for 10 min, washed and stained for 30 min in 0.37% alizarin red (Sigma), pH 4.1, washed again and air-dried. Alkaline phosphatase staining was performed using the leukocyte alkaline phosphatase kit (Sigma) following the manufacturer's instructions. Chondrocyte pellets were washed in PBS and fixed in 4% PFA, embedded in O.C.T. and mounted onto glass slides. Fixed and mounted chondrocyte slides were stained with H&E and alcian blue. Stained cells were analyzed on an Olympus BX51 microscope.

FGF2 ELISA. Cells were plated at 3,000/cm$^2$ and cultured in maintenance medium (DMEM, 1 g/l glucose, 10% FCS, 2 mM L-glutamine, 50 U/ml penicillin and 50 µml streptomycin) for 4 days as per our previous methods[2], whereupon media and matrix bound proteins were removed and FGF2 levels measured using an FGF2 Quantikine ELISA in accord with the manufacturer's recommendations (R&D Systems).

RNA purification and relative-quantitative-PCR. Total RNA from carry-on cultures, adipocytes and osteoblasts were purified using a Nucleospin II kit (Macherey-Nagel). Chondrocyte pellets were washed with PBS, treated with collagenase II & IV, collected by centrifugation, resuspended in Trizol (Invitrogen) and the RNA isolated. RNA quality and concentration was assessed and 0.5 µg used for reverse transcription using Superscript III polymerase (Invitrogen) as per the manufacturer's recommendations. FIG. 25 shows the Taqman primer/probes used for quantitative PCR. Primers and probes were designed using Primer express (Applied Biosystems) and synthesized by Proligo. Probe sequences were modified to dual labeled LNA (FAM/BHQ-1) hybridization probes, (in the table upper case letters in the probe sequences shows LNA nucleotides). Dual labeled MGB (VIC/TAMRA) labeled 18S rRNA primer probes were used as control for all reactions. All PCR reaction products were analyzed by agarose gel electrophoresis and sequenced to verify the specificity of the amplicon. Each quantitative PCR reaction (20 µl total) contained 80 ng cDNA (see materials and methods), 300 mM forward and reverse primer, 250 µM probe (100 µM Collagen2a1 probe was the only exception) and 10 µl Taqman Universal master mix (Applied Biosystems). Detection of 18S rRNA was performed in a similar way using 50 nM forward and 50 nM reverse primer and 100 nM probe. Quantitative PCR reactions were performed in triplicates on an ABI Prism 7000 sequence detection system (Applied Biosystems), with an initial 10 min activation step at 95° C. followed by 45 cycles of 95° C. for 20 sec; 55° C. for 10 sec, 60° C. for 30 sec and 72° C. for 40 sec. Relative expression units were calculated by normalizing the $2^{(-Dct)}$ values of the gene to the $2^{(-Dct)}$ values of 18S and multiplied by $10^6$.

Singular Value Decomposition

This forms the basis for a linear projection of a dataset onto a new reduced dimensional space that captures the maximum information present in the original data (that is, a principal components analysis).

Locally-Weighted Regression (LOESS) normalization for Stem Cell Array Data. Intensity measurements which are derived from gene hybridization-based technologies are often subject to variations across the gene chips that prevent meaningful comparisons of individual genes. These cross-chip variations necessitated adjustments of the chip intensities to a common distribution. A widely used alternative to scaling intensities by a constant global difference in hybridization is to fit an additive linear-model to the log-transformed gene intensity values using a LOESS smoothing function[3]. The fitted intensities are then used to infer differential expression.

Figure 27:
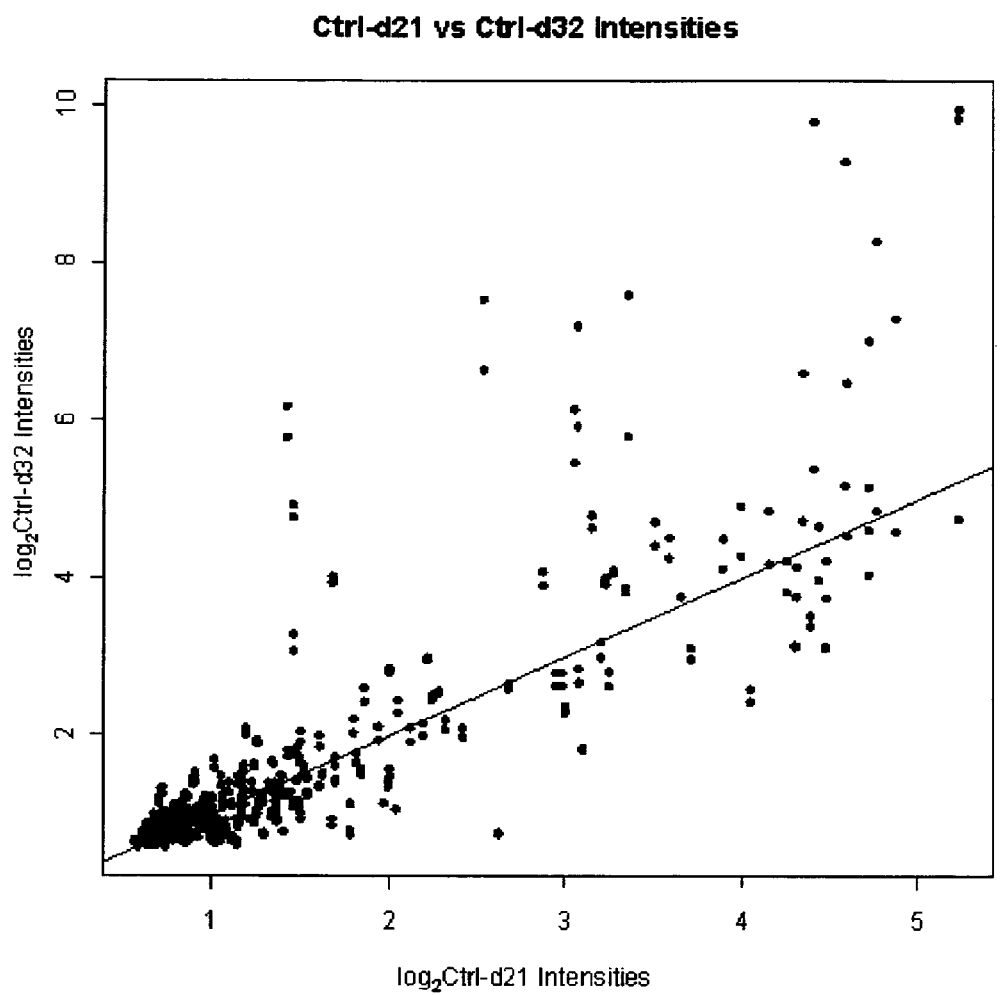
FIG. 27. Data plots after locally-weighted smoothing. Data colored as in Supplementary FIG. 26.

We first examined the effects of varying the neighborhood parameter, α, on the smoothing function through comparisons between controls. No radical shifts in the curvature of data plots were observed for ranges of 0.2≤α≤0.8. A conservative value, α=0.2, was then selected and applied to all arrays. MA plots reveal only a moderate degree of shift in the plot (See FIG. 27 for Ctrl-d21 vs Ctrl-d32) with effects that are more pronounced for extreme values of differential expression (FIG. 27-29).

Singular Value Decomposition of Stem Cell Array Data. The gene expression microarray data used in these experiments are high-dimensional datasets involving hundreds of genes and their co-expressions. Despite this seeming complexity, most of the important molecular information differentiating between HS-2 and controls actually exist as a number of simple and fundamental patterns. We wish to discover the most informative patterns (or singular vectors) within the dataset and use them to derive robust definitions for the effects of HS-2 on sternness through singular value decomposition.

A matrix, A, which represents stem cell array data consisting of m separate experimental conditions (treatments of heparan sulfate vs controls) on the rows and n variables (genes on each array) on the columns is first pre-processed by taking its covariance matrix prior to singular value decomposition[4]. The matrix is decomposed as follows:

$$A_{(n \times n)} = U_{(n \times n)} S_{(n \times n)} V'_{(n \times n)} \quad (1)$$

where S is a diagonal matrix consisting of the singular values $(\lambda_1, \lambda_2 \ldots \lambda_n)$ of matrix A'A (A' denotes the transpose of A). The columns of U and V are respectively the singular vectors corresponding to the matrices A'A and AA'. Both U and V are orthogonal matrices so that projections, C, onto these vectors is given as follows:

$$C = USV'V = AV = US \quad (2)$$

The proportion of variance associated with the first t vectors, $Var_t$, is therefore given by:

$$Var_t = \frac{\sum_{i=1}^{t} \lambda_i}{\sum_{i=1}^{n} \lambda_i} \quad (3)$$

Each singular value therefore represents the amount of variation associated with each singular vector (sets of genes) that distinguishes between the samples. Each component of the singular vector, the factor loadings, are therefore an expression of the importance of, each gene in the distinction:

$$p_{ij} = v_{ij} \quad (4)$$

Where $p_{ij}$ is the contribution of the ith gene to the j-th component and $v_{ij}$ is the i-th component of the j-th singular vector.

Figure 30:
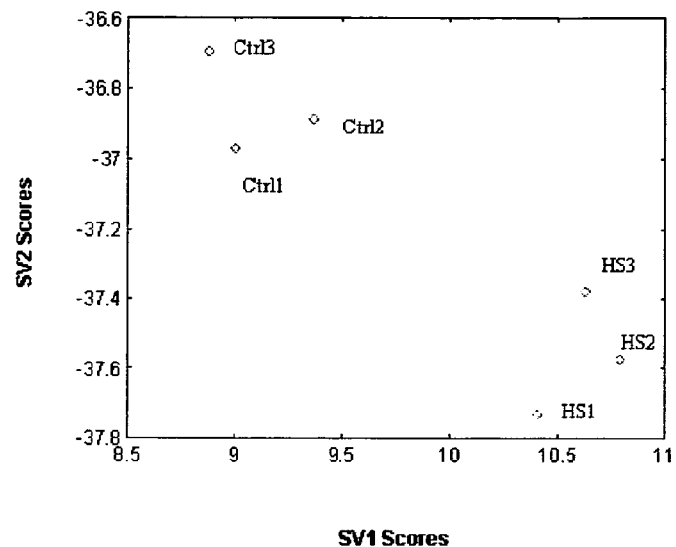
FIG. 30. Projection of the three hMSC patient pools after 21 days of culture in control, HS-2 containing media based on identified biomarkers. Controls (red circles) are distinguished from HS (green circles). (Pool 1, 2 and 3, hMSC1, 2 and 3 respectively (FIG. 23)).

Previous research has shown that genes with the highest factor loadings (FIG. 28) are greatly distanced from the origin and share similar characteristics in 2-D loading plots (FIG. 30). Several groups of potential sternness markers were defined based on positions in the loading plot. We examined the efficacy of using the top 90th-percentile distant genes by reconstructing the SVD using only these genes. The score plot revealed a clear separation of HS-2 and control in all 3 samples (FIG. 30). These results support the usefulness of SVD for separation and classification of samples.

Stability of SVD Projection Scores Assessed by Statistical Resampling. In addition to defining markers for stemness, we performed an additional validation of the SVD technique through statistical resampling. This is to evaluate the robustness of stemness signatures and clustering effects based on SVD scores. A natural criterion for the distance between any pair of samples, $C_a, C_b \in R^P$ under an SVD projection on the first P singular vectors is given by the following Euclidean metric in $R^P$:

$$\|L\|_p = \left( \sum_{i=1}^{p} |C_{ai} - C_{bi}|^p \right)^{1/p} \quad (5)$$

This metric avoids errors produced by arbitrary changes in the sign of eigenvectors of any particular axes resulting from axis reflections when raw projection scores are used[5]. As the Eigen values of the first 2 singular vectors constitute approximately 70% of variance, we have chosen P=2.

Gene expression measurements may often be affected by errors introduced during capture of luminence intensities leading to an artificial inflation or deflation of individual intensity values in a non-systematic fashion. To determine the significance of clustering effects for the various treatment conditions under an SVD projection and their effects on stemness therefore requires the derivation of a statistical framework for estimation of variance in projection scores in the presence of outliers. We formally modeled this variation (rather than base comparisons against randomly-generated data[6]) through the use of a non-parametric bootstrap[7]. The method more accurately approximates parameters of interest, is tolerant of violations of normality and equivariance assumptions in real data that adversely affect other parametric multivariate approaches and has therefore been found suitable for application under diverse contexts in gene expression[8,9]. Following an established procedure[10], given A, we construct A* by drawing with replacement the $a_i^*$, computing (5) for a total of B iterations. Given the computationally intensive nature of the SVD, we have chosen B=1000.

Figure 31:
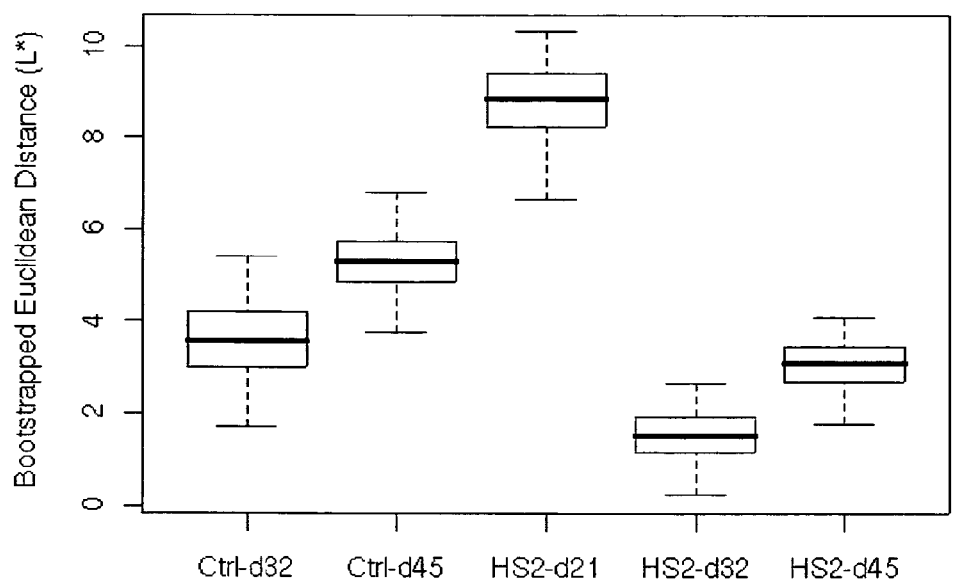
FIG. 31. Bootstrapped Euclidean distances between sample projection scores. Distributions were approximately normal (median distances at centre of upper and lower quartiles). Dashes denote adjacent values located interquartile distant from upper and lower quartiles. Only comparisons with respect to Ctrl-d21 are shown. HS distances of later passages were essentially non-overlapping with respect to control distances.

A parallel boxplot of the distribution of L* for each sample with respect to Ctrl-d21 shows an approximate normal distribution (FIG. 31). We derived estimates of the percentiles of a Student's t-statistic for each pair of distances, T*, as follows[11]:

$$T^* = \frac{L^* - \hat{L}}{\hat{\sigma}^*} \quad (6)$$

Where $\hat{L}$, $\hat{\sigma}$, L* and $\sigma^*$ are the observed values of L, its standard error, a bootstrap estimate of L and its corresponding bootstrap standard error estimate respectively. The percentiles, $T^{*(0.95)}$ and $T^{*(0.05)}$ therefore give the bootstrap-t approximate confidence intervals:

$$L \in [\hat{L} - \hat{\sigma} T^{*(0.95)}, \hat{L} - \hat{\sigma} T^{*(0.05)}] \quad (7)$$

Bootstrapped confidence estimates for L are listed in FIG. 32. All mathematical computations were implemented in MATLAB (Mathworks Inc, Natick, Mass.) and R (www.r-project.org). HS-2-d32 or even HS-2-d45 bootstrap intervals are much smaller with respect to Ctrl-d21 than any other treatments. The results indicate that clustering effects on SVD scores are robust even in the presence of noise. Overall, this supports the notion that the clustering of HS-2 samples with controls of earlier passages indicates an effect of HS-2 treatments on preservation of stemness.

References To Supplementary Methods
1. Li, W- J., Tuli R., Huang X, Laquerriere P. and Tuan R S. Multilineage differentiation of human mesenchymal stem cells in a three-dimensional nanofibrous scaffold. *Biomaterials* 26, 5158-5166 (2005)
2. Rider, D. A., Dombrowski, C., Sawyer, A. A., Ng, G. H., Leong, D., Hutmacher, D. W., Nurcombe, V. and Cool, S. M. Autocrine fibroblast growth factor 2 increases the multipotentiality of human adipose-derived mesenchymal stem cells. *Stem Cells* 26, 1598-1608 (2008).
3. Cleveland, W. S. Robust locally weighted regression and smoothing scatterplots. *J. Amer. Stat. Assoc.* 74, 829-836 (1979).
4. Raychaudhuri, S., Stuart, J. M. & Altman, R. B. Principal components analysis to summarize microarray experiments: application to sporulation time series. *Pac. Symp. Biocomput.* 455-66 (2000).
5. Peres-Neto, P. R., Jackson, D. A. & Somers, K. M. Giving meaningful interpretation to ordination axes: Assessing loading significance in principal component analysis. *Ecology.* 84(9), 2347-2363 (2003).
6. Ghosh, D. Resampling methods for variance estimation of singular value decomposition analyses from microarray experiments. *Funct. Integr. Genomics.* 2(3), 92-7 (2002).
7. Kerr, K. & Churchill, G. A. Bootstrapping cluster analysis: Assessing the reliability of conclusions from microarray experiments. *Proc. Natl. Acad. Sci. USA.* 98(16), 8961-8966 (2001).
8. Tseng, G. C. & Wong, W. W. Tight clustering: A resampling-based approach for identifying stable and tight patterns in data. *Biometrics.* 61(1), 10-6 (2005).
9. Efron, B. & Tibshirani, R. J. An Introduction to the Bootstrap. (Chapman and Hall, New York 1993).
10. Besse, P. & De Falguerolles, A. In Computer Intensive Methods in Statistics (eds Hardie, W. & Simar, L.) 167-176 (Springer, New York, 1993).
11. Efron, B. & Tibshirani, R. J. In Advances in Biometry: 50 years of the International Biometric Society (eds Armitage, P. & David, H. A.) 131-149 (Wiley, New York, 1996).

The invention claimed is:

1. A method of treating a bone fracture in a subject, the method comprising administering to the subject a therapeutically effective amount of mesenchymal stem cells obtained by culture in the presence of HS-2.

2. The method of claim 1 wherein the method is a method of enhanced mesenchymal stem cell mediated fracture repair, the method involving improvement in the speed of fracture repair relative to the speed of fracture repair obtained through treatment with mesenchymal stem cells obtained by culture in the absence of HS-2.

3. The method of claim 1 wherein prior to administration of mesenchymal stem cells, the method comprises culturing stem cells in contact with HS-2 so as to produce said therapeutically effective amount of mesenchymal stem cells.

4. The method of claim 3 further comprising the step of formulating said therapeutically effective amount of mesenchymal stem cells as a pharmaceutical composition comprising mesenchymal stem cells obtained by culture in the presence of HS-2 and a pharmaceutically acceptable carrier, adjuvant or diluent, wherein the pharmaceutical composition is administered to the subject.

5. The method of claim 1 wherein the method comprises administering the mesenchymal stem cells to tissue surrounding the fracture.

6. The method of claim 1 wherein administration of the mesenchymal stem cells comprises injecting the mesenchymal stem cells into tissue surrounding the fracture.

7. A method of treating a bone fracture in a subject, the method comprising surgically implanting a biocompatible implant or prosthesis into tissue of the subject at or surrounding the site of fracture, which implant or prosthesis comprises a biomaterial and mesenchymal stem cells obtained by culture in the presence of HS-2.

8. The method of claim 7 wherein the implant or prosthesis is coated with mesenchymal stem cells obtained by culture in the presence of HS-2.

9. The method of claim 7 wherein the implant or prosthesis is impregnated with mesenchymal stem cells obtained by culture in the presence of HS-2.

10. The method of claim 2 wherein prior to administration of mesenchymal stem cells, the method comprises culturing stem cells in contact with HS-2 so as to produce said therapeutically effective amount of mesenchymal stem cells.

11. The method of claim 2 wherein the method comprises administering the mesenchymal stem cells to tissue surrounding the fracture.

12. The method of claim 2 wherein administration of the mesenchymal stem cells comprises injecting the mesenchymal stem cells into tissue surrounding the fracture.

13. The method of claim 3 wherein the method comprises administering the mesenchymal stem cells to tissue surrounding the fracture.

14. The method of claim 3 wherein administration of the mesenchymal stem cells comprises injecting the mesenchymal stem cells into tissue surrounding the fracture.

15. The method of claim 4 wherein the method comprises administering the pharmaceutical composition to tissue surrounding the fracture.

16. The method of claim 4 wherein administration of the pharmaceutical composition comprises injecting the pharmaceutical composition into tissue surrounding the fracture.

* * * * *